US009669090B2

(12) United States Patent
Mannie

(10) Patent No.: US 9,669,090 B2
(45) Date of Patent: *Jun. 6, 2017

(54) CYTOKINES AND NEUROANTIGENS FOR TREATMENT OF IMMUNE DISORDERS

(71) Applicant: East Carolina University, Greenville, NC (US)

(72) Inventor: Mark D. Mannie, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/518,705

(22) Filed: Oct. 20, 2014

(65) Prior Publication Data
US 2015/0104414 A1    Apr. 16, 2015

Related U.S. Application Data

(63) Continuation of application No. 13/262,039, filed as application No. PCT/US2010/029350 on Mar. 31, 2010, now abandoned.

(60) Provisional application No. 61/165,367, filed on Mar. 31, 2009.

(51) Int. Cl.
| | |
|---|---|
| *A61K 39/00* | (2006.01) |
| *A61K 39/39* | (2006.01) |
| *A61K 38/17* | (2006.01) |
| *A61K 38/21* | (2006.01) |
| *C07K 14/47* | (2006.01) |
| *C07K 14/565* | (2006.01) |
| *C12N 9/64* | (2006.01) |

(52) U.S. Cl.
CPC .......... *A61K 39/39* (2013.01); *A61K 38/1709* (2013.01); *A61K 38/21* (2013.01); *A61K 38/215* (2013.01); *A61K 39/0008* (2013.01); *C07K 14/4713* (2013.01); *C07K 14/565* (2013.01); *C12N 9/6424* (2013.01); *A61K 2039/54* (2013.01); *A61K 2039/55522* (2013.01); *A61K 2039/577* (2013.01); *A61K 2039/6031* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,814,485 | A | 9/1998 | Dorin et al. |
| 7,442,546 | B2 | 10/2008 | Humes |
| 7,674,884 | B2 | 3/2010 | Elson et al. |
| 7,759,367 | B2 | 7/2010 | Smith |
| 2004/0013644 | A1 | 1/2004 | Rasmussen et al. |
| 2007/0275899 | A1 | 11/2007 | Garren et al. |
| 2008/0064859 | A1 | 3/2008 | Vandenbark et al. |
| 2008/0095766 | A1 | 4/2008 | Koenig et al. |
| 2008/0233132 | A1 | 9/2008 | Miller et al. |

FOREIGN PATENT DOCUMENTS

| | | |
|---|---|---|
| EP | 0326120 A2 | 8/1989 |
| WO | WO 91/01146 A | 2/1991 |
| WO | WO 01/68896 A | 9/2001 |
| WO | WO 03/024404 A | 3/2003 |
| WO | WO 2004/092210 A | 10/2004 |
| WO | WO 2006/063800 A | 6/2006 |
| WO | WO 2008/130382 A2 | 10/2008 |

OTHER PUBLICATIONS

Kim et al. "An ovalbumin-IL-12 fusion protein is more effective than ovalbumin plus free recombinant IL-12in inducing a T helper cell type 1-dominated immune response and inhibiting antigen-specific IgE production", *J. of Immunology* 158(9):4137-4144 (1997).
Lim et al. "Potentiation of antigen-specific, Th1 immune responses by multiple DNA vaccination with an ovalbumin/interferon-gamma hybrid construct", *Immunology* 94(2):135-141 (1998.
Kim et al. "Efficient induction of antigen-specific T helper type 1-mediated immune responses by intramuscular injection with ovalbumin/interleukin-18 fusion DNA", *Vaccine, Butterworth Scientific* 19(30):4107-4114 (2001).
Maecker et al. "Vaccination with allergen-IL-18 fusion DNA protects against, and reverses established, airway hyperreactivity in a murine asthma model", *J. of Immunology* 166(2):959-965 (2001).
Martin et al. "Protective effect of the interleukin-1 receptor antagonist (IL-1ra) on experimental allergic encephalomyelitis in rats", *J. of Neuroimmunology*, 61(2):241-245.
Wang et al. "Adenovirus expressing interleukin-1 receptor antagonist alleviates allergic airway inflammation in a murine model of asthma", *Gene Therapy* 13(19):1414-1421 (2006).
Rafei et al. "A GMCSF and IL-15 Fusokine Leads to Paradoxical Immunosuppression in Vivo Via Asymmetrical JAK/STAT Signaling Through the IL 15 Receptor Complex"*Blood* 109(5):2234-2242 (2007).
Rafei et al. "A Granulocyte-Macrophage Colony-Stimulating Factor and Interleukin-15 Fusokine Induces a Regulatory B Cell Population With Immune Suppressive Properties" *Nature Medicine* Advanced Online Publication pp. 1-9 (2009).
Kim et al. "Covalent Linkage of IL-12 and Ovalbumin Confines the Effects of IL-12 to Ovalbumin-specific Immune Response", *Arch. Pharm. Res.* 20(5):396-403 (1997).
Mannie et al. IL-2/Neuroantigen Fusion Proteins as Antigen-Specific Tolerogens in Experimental Autoimmune Encephalomyelitis (EAE): Correlation of T Cell-Mediated Antigen.

(Continued)

*Primary Examiner* — Marianne P Allen
(74) *Attorney, Agent, or Firm* — Myers Bigel, P.A.

(57) ABSTRACT

The present invention provides methods of regulating an immunological disorder comprising administering to a subject an effective amount of (i) an autoimmune antigen in conjunction with (ii) an anti-inflammatory cytokine. Compositions including the same are also provided.

3 Claims, 8 Drawing Sheets

(56) References Cited

OTHER PUBLICATIONS

Dasgupta et al. "Myelin Basic Protein-primed T Cells of Female but Not Male Mice Induce Nitric-oxide Synthase and Proinflammatory Cytokines in Microglia", *J. Biological Chem.* 280(38):32609-32617 (2005).

Goodin "Treatment of Multiple Sclerosis with Human Beta Interferon", *The Int. MS Journal* 12:96-108 (2005).

Xu et al. "Suppression of ongoing experimental allergic encephalomyelitis (EAE) in Lewis rats: synergistic effects of myelin basic protein (MBP) peptide 68-86 and IL-4", *Clin Exp. Immunol* 120:526-531 (2000).

Bork "Powers and Pitfalls in Sequence Analysis: The 70% Hurdle", *Genome Research* 10:398-400 (2000).

Crystal "Transfer of Genes to Humans: Early Lessons and Obstacles to Success", *Science* 270:404-410 (1995).

Doerks et al. "Protein annotation: detective work for function prediction", *Trends in Genetics* 14(6):248-250 (1998).

Junegst "What next for human gene therapy?", *British Medical Journal* 326:1410-1411 (2003).

Kaufman et al. "Transgenic Analysis of a 100-kb Human beta-Globin Cluster-Containing DNA Fragment Propagated as a Bacterial Artificial Chromosome", *Blood* 94:3178-3184 (1999).

Marshall "Gene Therapy's Growing Pains", *Science* 269(5227):1050-1055 (1995).

Rubanyi "The future of human gene therapy", *Molecular Aspects of Medicine* 22:113-142 2001.

Skolnick et al. "From genes to protein structure and function: novel applications of computational approaches in the genomic era", *Trends in Biotech.* 18(1):34-39 (2000).

Tokuriki et al. "Stability effects of mutations and protein evolvability", *Current Opinion in Structural Biology* 19:596-604 (2009).

Verma et al. "Gene therapy—promises, problems and prospects", *Nature* 389:239-242 (1997).

Wang et al. "Rapid analysis of gene expression (RAGE) facilitates universal expression profiling", *Nucleic Acids Research* 27(23):4609-4618 (1999).

Wells "Additivity of Mutational Effects in Proteins", *Biochemistry* 29(37):8509-8517 (1990).

US 9,669,090 B2

CYTOKINES AND NEUROANTIGENS FOR TREATMENT OF IMMUNE DISORDERS

RELATED APPLICATION DATA

This application is a continuation application of U.S. application Ser. No. 13/262,039, filed Dec. 12, 2011 which is a 35 U.S.C. §371 national phase application of PCT International Application No. PCT/US2010/029350, filed Mar. 31, 2010, which claims priority to U.S. Provisional Patent Application Ser. No. 61/165,367, filed Mar. 31, 2009. The disclosures of each application are incorporated herein by reference in their entireties. The above PCT International Application was published on Oct. 14, 2010 as International Publication No. WO 2010/117848 A1.

STATEMENT REGARDING THE ELECTRONIC FILING OF SEQUENCES

A sequence listing in ASCII text format, submitted under 37 C.F.R. §1.821, entitled 5218-182TSCT_ST25.txt, 3,852 bytes in size, generated on Oct. 16, 2014, and filed electronically via EFS-Web, is provided in lieu of a paper copy.

FIELD OF THE INVENTION

The present invention relates to methods of inducing immunological tolerance and methods of treating immunological disorders, for example, autoimmune diseases, allergic diseases, and transplant rejection.

BACKGROUND OF THE INVENTION

Multiple sclerosis (MS) is a demyelinating inflammatory disease of the central nervous system myelin that afflicts well over 2 million people in the Western world (Cassan, C., and R. S. Liblau. 2007. Immune tolerance and control of CNS autoimmunity: from animal models to MS patients. *J Neurochem* 100:883-892; McFarland, H. F., and R. Martin. 2007. Multiple sclerosis: a complicated picture of autoimmunity. *Nat Immunol* 8:913-919; and Hauser, S. L., and J. R. Oksenberg. 2006. The neurobiology of multiple sclerosis: genes, inflammation, and neurodegeneration. *Neuron* 52:61-76). Although the etiology of MS is currently unknown, substantial evidence indicates that autoimmune responses may be a factor for initiation and progression of the disease. Interferon-beta (IFN-β) is currently used as a mainstream therapy for MS (Javed, A., and A. T. Reder. 2006. Therapeutic role of beta-interferons in multiple sclerosis. *Pharmacol Ther* 110:35-56; Borden, E. C., G. C. Sen, G. Uze, R H. Silverman, R. M. Ransohoff, G. R. Foster, and G. R. Stark. 2007. Interferons at age 50: past, current and future impact on biomedicine. *Nat Rev Drug Discov* 6:975-990; and Tourbah, A., and O. Lyon-Caen. 2007. Interferons in multiple sclerosis: ten years' experience. *Biochimie* 89:899-902). IFN-β is considered a disease-modifying treatment that can reduce subclinical disease measured by magnetic resonance imaging (MRI) although the clinical benefit reflects an approximate 30% reduction in the attack rate.

Aside from the modest efficacy of IFN-β, the drug has disadvantages including high costs and substantial inter-patient variability in tolerability and efficacy. Also, IFN-β most likely inhibits MS through modulation of general regulatory pathways rather than by specifically disabling pathogenic clonotypes. Because IFN-β generally inhibits autoimmune responses without causing immunological tolerance, IFN-β is typically chronically self-administered as an injection for a lifetime.

Experimental autoimmune encephalomyelitis (EAE) is a widely studied animal model of MS and has helped to shape the current understanding of the pathophysiology of MS (Gold, R., C. Linington, and H. Lassmann. 2006. Understanding pathogenesis and therapy of multiple sclerosis via animal models: 70 years of merits and culprits in experimental autoimmune encephalomyelitis research. *Brain* 129: 1953-1971). Like MS, EAE is inhibited by administration of IFN-β. A substantial number of studies have shown that Type I interferons effectively inhibit EAE or experimental autoimmune neuritis when interferon-α/β is administered post-immunization during the induction or effector phases of disease (Abreu, S. L. 1982. Suppression of experimental allergic encephalomyelitis by interferon. *Immunol Commun* 11:1-7; Hertz, F., and R. Deghenghi. 1985. Effect of rat and beta-human interferons on hyperacute experimental allergic encephalomyelitis in rats. *Agents Actions* 16:397-403; Brod, S. A., M. Khan, R. H. Kerman, and M. Pappolla. 1995. Oral administration of human or murine interferon alpha suppresses relapses and modifies adoptive transfer in experimental autoimmune encephalomyelitis. *J Neuroimmunol* 58:61-69; Brod, S. A., M. Scott, D. K. Burns, and J. T. Phillips. 1995. Modification of acute experimental autoimmune encephalomyelitis in the Lewis rat by oral administration of type 1 interferons. *J Interferon Cytokine Res* 15:115-122; Yu, M., A. Nishiyama, B. D. Trapp, and V. K. Tuohy. 1996. Interferon-beta inhibits progression of relapsing-remitting experimental autoimmune encephalomyelitis. *J Neuroimmunol* 64:91-100; Brod, S. A., and M. Khan. 1996. Oral administration of IFN-alpha is superior to subcutaneous administration of IFN-alpha in the suppression of chronic relapsing experimental autoimmune encephalomyelitis. *J Autoimmun* 9:11-20; Vriesendorp, F. J., R. E. Flynn, M. Khan, M. A. Pappolla, and S. A. Brod. 1996. Oral administration of type I interferon modulates the course of experimental allergic neuritis. *Autoimmunity* 24:157-165; Yasuda, C. L., A. Al-Sabbagh, E. C. Oliveira, B. M. Diaz-Bardales, A. A. Garcia, and L. M. Santos. 1999. Interferon beta modulates experimental autoimmune encephalomyelitis by altering the pattern of cytokine secretion. *Immunol Invest* 28:115-126; Zou, L. P., D. H. Ma, L. Wei, P. H. van der Meide, E. Mix, and J. Zhu. 1999. IFN-beta suppresses experimental autoimmune neuritis in Lewis rats by inhibiting the migration of inflammatory cells into peripheral nervous tissue. *J Neurosci Res* 56:123-130; Tuohy, V. K., M. Yu, L. Yin, P. M. Mathisen, J. M. Johnson, and J. A. Kawczak. 2000. Modulation of the IL-10/IL-12 cytokine circuit by interferon-beta inhibits the development of epitope spreading and disease progression in murine autoimmune encephalomyelitis. *J Neuroimmunol* 111:55-63; and Floris, S., S. R. Ruuls, A. Wierinckx, S. M. van der Pol, E. Dopp, P. H. van der Meide, C. D. Dijkstra, and H. E. De Vries. 2002. Interferon-beta directly influences monocyte infiltration into the central nervous system. *J Neuroimmunol* 127:69-79).

The inhibitory mechanism of IFN-β is associated with altered immunoregulation, but no evidence exists to indicate that IFN-β causes an antigen-specific immunological tolerance. Endogenous IFN-β also appears to limit encephalitogenic responses where EAE is exaggerated in mice genetically deficient in IFN-β (Teige, I., A. Treschow, A. Teige, R. Mattsson, V. Navikas, T. Leanderson, R. Holmdahl, and S. Issazadeh-Navikas. 2003. IFN-beta gene deletion leads to augmented and chronic demyelinating experimental autoimmune encephalomyelitis. *J Immunol* 170:4776-4784; Teige, I., Y. Liu, and S. Issazadeh-Navikas. 2006. IFN-beta inhibits T cell activation capacity of central nervous system APCs. *J Immunol* 177:3542-3553) or the type I IFN receptor (Prinz, M., H. Schmidt, A. Mildner, K. P. Knobeloch, U. K. Hanisch, J. Raasch, D. Merkler, C. Detje, I. Gutcher, J. Mages, R. Lang, R. Martin, R. Gold, B. Becher, W. Bruck, and U. Kalinke. 2008. Distinct and Nonredundant In Vivo Functions of IFNAR on Myeloid Cells Limit Autoimmunity in the Central Nervous System. *Immunity*). Indeed, expression of the type I IFN receptor on myeloid cells appears to be a factor in the mechanism by which IFN-β controls encephalitogenic responses.

Antigen-specific therapies may be considered advantageous compared to general immunosuppressive strategies at least because the former has potential to cause specific immunological tolerance (Faria, A. M., and H. L. Weiner. 2006. Oral tolerance: therapeutic implications for autoimmune diseases. *Clin Dev Immunol* 13:143-157; Fontoura, P., H. Garren, and L. Steinman. 2005. Antigen-specific therapies in multiple sclerosis: going beyond proteins and peptides. *Int Rev Immunol* 24:415-446; and Sospedra, M., and R. Martin. 2005. Antigen-specific therapies in multiple sclerosis. *Int Rev Immunol* 24:393-413). Several antigen-specific therapies are being developed, including those based on altered peptide ligands, DNA vaccines, and mucosal antigen delivery.

Cytokine-antigen fusion proteins were originally developed for vaccination against cancer and infectious agents but have also been explored as tolerogenic vaccines based on the use of inhibitory, anti-inflammatory, or tolerogenic cytokines as the cytokine fusion partner (Mannie, M. D., and D. J. Abbott. 2007a. A fusion protein consisting of IL-16 and the encephalitogenic peptide of myelin basic protein constitutes an antigen-specific tolerogenic vaccine that inhibits experimental autoimmune encephalomyelitis. *J Immunol* 179:1458-1465 and Mannie, M. D., B. A. Clayson, E. J. Buskirk, J. L. DeVine, J. J. Hernandez, and D. J. Abbott. 2007b. IL-2/neuroantigen fusion proteins as antigen-specific tolerogens in experimental autoimmune encephalomyelitis (EAE): correlation of T cell-mediated antigen presentation and tolerance induction. *J Immunol* 178:2835-2843). Two cytokine-antigen fusion proteins in which the IL-2 or IL-16 cytokines were fused to the encephalitogenic determinant of MBP (i.e., IL2-NAg or NAg-IL16) have successfully been used to prevent a subsequent encephalitogenic sensitization and to treat ongoing EAE (WO 2008/13082).

However, it remains desirable to have additional antigen-specific therapies for the treatment of immunological disorders.

SUMMARY OF THE INVENTION

Antigen-specific therapies may provide advantages, particularly in the possibility that a time-limited series of administrations may cause an enduring cessation of auto-aggressive immunological attacks. A central goal of contemporary immunological research is the induction of antigen-specific tolerance as a means to re-establish self tolerance to auto-antigens in human autoimmune diseases. As described herein, IFN-β acts as a tolerogenic adjuvant, a tolerogenic fusion partner as well as a tolerogenic adjuvant in therapy employing an autoimmune antigen or a cytokine-autoimmune antigen fusion protein thereby providing significant implications for development of tolerogenic vaccines.

Accordingly, embodiments of the present invention provide methods of regulating an immunological disorder including administering to a subject an effective amount of (i) an autoimmune antigen or portion thereof in conjunction with (ii) an anti-inflammatory cytokine, with the proviso that (i) and (ii) do not comprise a fusion protein. That is, in some embodiments, the autoimmune antigen or portion thereof in conjunction with an anti-inflammatory cytokine is not a fusion protein. In particular embodiments, the present invention provides administration of (i) an encephalitogenic determinant portion of a myelin basic protein (MBP) in conjunction with (ii) an anti-inflammatory cytokine such as IFN-β, wherein (i) and (ii) are administered simultaneously or sequentially with the proviso that (i) and (ii) do not comprise a fusion protein.

Embodiments of the present invention further provide methods of regulating an immunological disorder including administering to a subject an effective amount of (a) a fusion protein comprising an autoimmune antigen or portion thereof, an optional enterokinase linking moiety and an anti-inflammatory cytokine, and (b) an anti-inflammatory cytokine. In particular embodiments, the fusion protein comprises an encephalitogenic determinant portion of a myelin basic protein, an optional enterokinase linking moiety comprising amino acids of SEQ ID NO: 2, and an anti-inflammatory cytokine such as IFN-β.

Embodiments of the present invention also provide compositions including (a) an autoimmune antigen or portion thereof, (b) an anti-inflammatory cytokine, and (c) a pharmaceutically acceptable carrier, excipient or diluent, with the proviso that (a) and (b) do not comprise a fusion protein. In particular embodiments, the composition includes an encephalitogenic determinant portion of a myelin basic protein and IFN-β.

Embodiments of the present invention provide compositions including (a) at least one fusion protein comprising an autoimmune antigen or portion thereof, optionally an enterokinase linking moiety comprising amino acids of SEQ ID NO: 2 and an anti-inflammatory cytokine, (b) an anti-inflammatory cytokine, and (c) a pharmaceutically acceptable carrier, excipient or diluent. In particular embodiments, the fusion protein comprises an encephalitogenic determinant portion of a myelin basic protein, an optional enterokinase linking moiety comprising amino acids of SEQ ID NO: 2, and an anti-inflammatory cytokine such as IFN-β.

Embodiments of the present invention further provide immunogenic compositions including the active agents described herein.

Embodiments of the present invention provide methods of modulating an immune response including administering the compositions described herein in an amount sufficient to elicit a tolerogenic response.

Embodiments of the present invention provide kits including one or more containers having pharmaceutical dosage units including an effective amount of the compositions described herein, wherein the container is packaged with optional instructions for the use thereof.

Embodiments of the present invention provide methods of modulating antigen-presenting cell function including exposing an antigen-presenting cell to a composition as described herein.

Embodiments of the present invention provide uses of the compositions described herein for the preparation of a medicament for carrying out the utilities described herein.

The foregoing and other objects and aspects of the present invention are explained in greater detail in reference to the drawings and description set forth herein.

BRIEF DESCRIPTION OF THE DRAWINGS

FIG. 7B shows data from 7A normalized to 100% for each curve. These data are representative of two independent experiments.

DETAILED DESCRIPTION

Figure 1:
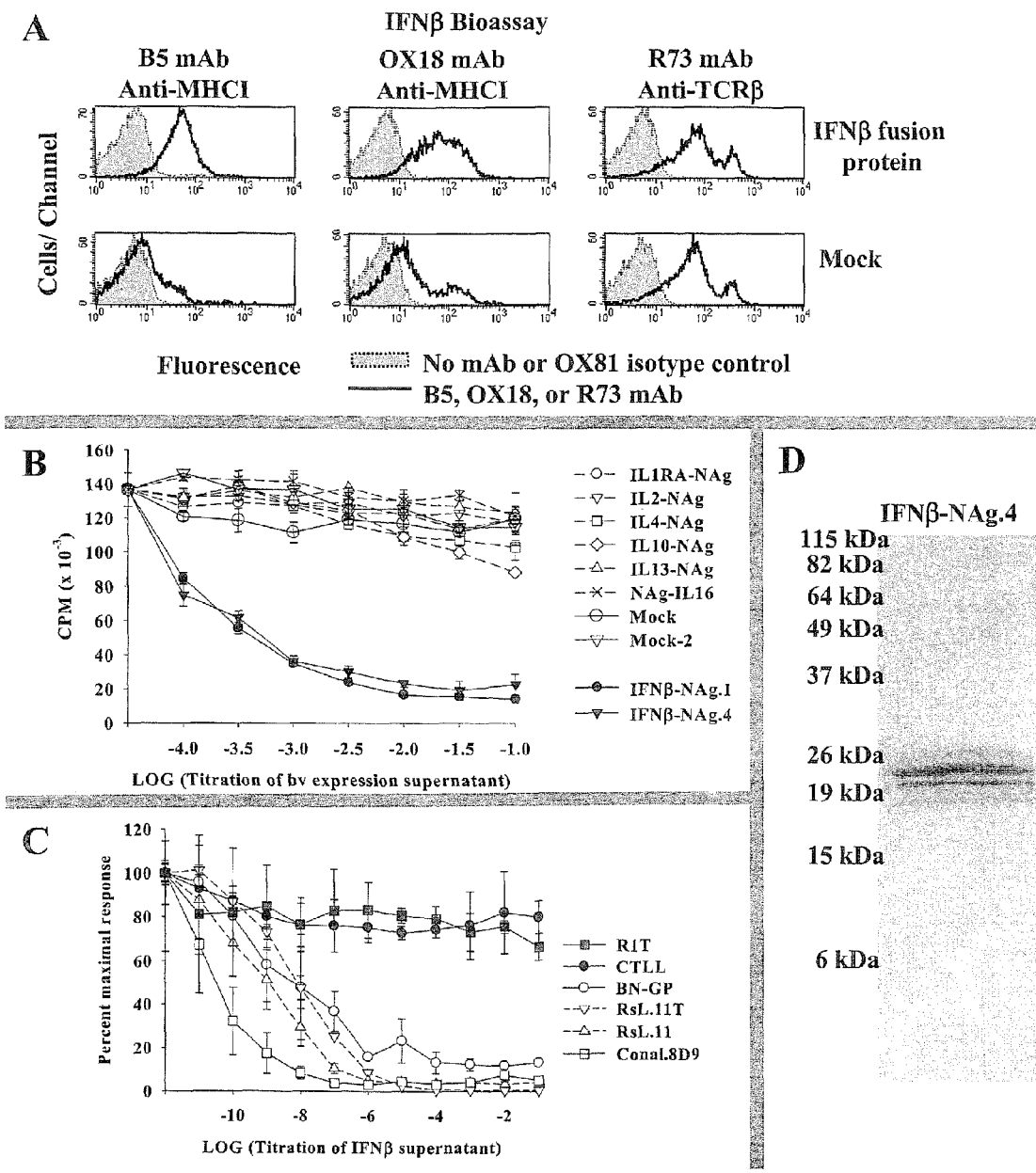
FIG. 1. The IFNβ-NAg his-tagged fusion protein was biologically active and was purified on nickel resins. (A) To assess whether IFNβ-NAg induced class I MHC expression, thymocytes (5×10$^6$/ml in complete RPMI) were cultured with or without IFNβ-NAg for 2 days and then were stained with B5 (anti-MHC-I), OX18 (anti-MHC-I), R73 (anti-TCRβ), or OX81 (anti-IL4; isotype control) and were analyzed by flow cytometry. (B) To assess IFNβ-mediated anti-proliferative activity, supernatants from two independently derived IFNβ-NAg expression systems as well as supernatants from several control expression systems were added at designated titrations (x-axis) to IL-2 stimulated cultures of BN-GP T cells. (C) To assess the specificity of anti-proliferative activity, baculovirus supernatants containing IFNβ-NAg were added at designated titrations to cultures of rat (R1T, BN-GP, RsL.11T, RsL.11, or Conal.8D9) or mouse (CTLL) T cells. Proliferative assays (B & C) were pulsed with [$^3$H]thymidine on the second day of a 3-day culture. (D) Shown is a representative SDS-PAGE analysis of purified IFNβ-NAg. These data are representative of at least three independent experiments.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods can be used for the production of viral and non-viral vectors, manipulation of nucleic acid sequences, production of transformed cells, and the like according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, and other references mentioned herein are incorporated by reference in their entirety.

1. DEFINITIONS

As used herein, "a" or "an" or "the" can mean one or more than one. Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

Moreover, the present invention also contemplates that in some embodiments of the invention, any feature or combination of features set forth herein can be excluded or omitted.

The term "modulate," "modulates" or "modulation" refers to enhancement (e.g., an increase) or inhibition (e.g., a reduction) in the specified activity.

The term "regulate" as used herein refers to the ability to affect a method, process, state of being, disorder or the like. The effect may be that of prevention, treatment or modulation.

By the terms "treat," "treating" or "treatment of," it is intended that the severity of the disorder or the symptoms of the disorder are reduced, or the disorder is partially or entirely eliminated, as compared to that which would occur in the absence of treatment. Treatment does not require the achievement of a complete cure of the disorder and can refer to stabilization of disease.

By the terms "preventing" or "prevention", it is intended that the inventive compounds, compositions and/or methods eliminate or reduce the incidence or onset of the disorder, as compared to that which would occur in the absence of the measure taken. Alternatively stated, the present methods slow, delay, control, or decrease the likelihood or probability of the disorder in the subject, as compared to that which would occur in the absence of the measure taken.

A "therapeutically effective" or "effective" amount is intended to designate a dose that causes a relief of symptoms of a disease or disorder as noted through clinical testing and evaluation, patient observation, and/or the like. "Effective amount" or "effective" can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms and body weight of the patient but also depending upon the compound (or composition which is used interchangeably unless otherwise specified or inappropriate for the circumstances) being administered.

As used herein, the administration of a compound "in conjunction with" another compound means that the two compounds are administered closely enough in time that the presence of one alters the biological effects of the other. The two compounds may be administered in conjunction simultaneously (i.e., concurrently) or sequentially. Simultaneous administration may be carried out by mixing the compounds prior to administration and providing the same as a mixture, by administering the compounds at the same point in time but at different anatomic sites or using different routes of administration. Sequential administration can be carried out by administering one of the compounds prior to or before the other, and consequently, administering one of the compounds after the other.

"Immune response" generally refers to innate and acquired immune responses including, but not limited to, both humoral immune responses (mediated by B lymphocytes) and cellular immune responses (mediated by T lymphocytes). An immune response may be beneficial and lead to immunity against infectious pathogens, or an immune response may be pathogenic and lead to autoimmune or hypersensitivity disease. Immune responses against foreign viruses, bacteria, fungi, parasites typically represent beneficial adaptive immune responses. Immune responses against self tissues, innocuous foreign objects (e.g., dust mite or pollen allergens, etc.), or tissue transplants represent examples of adverse maladaptive immune responses.

The term "antigen" as used herein means a substance or compound that stimulates an immune response. Although usually a protein or polysaccharide, antigens may be any type of molecule, which can include small molecules (haptens) that are coupled to a carrier-protein.

As used herein, the term "autoimmune antigen" refers to any self protein or self component that serves either as a target or cause of an autoimmune disease. Examples of autoimmune antigens include, but are not limited to, myelin basic protein, proteolipid protein, or myelin oligodendrocyte protein (multiple sclerosis); peripheral myelin proteins P0 and P2 (Guillain-Barre syndrome); acetylcholine receptor (myasthenia gravis); cardiac myosin (rheumatic fever/myocarditis); proteins of the beta cells in the Isles of Langerhans—GAD (glutamic acid decarboxylase), insulin (Type I autoimmune diabetes mellitus), the thyroid-stimulating hormone receptor (Grave's disease), platelets (thrombocytopenic purpura), neuromuscular junction (myasthenia gravis), red blood cells (autoimmune hemolytic anemia and intracellular antigens (spliceosomes, ribosomes, nucleic acid, etc in systemic lupus erythematosus).

As used herein, the term "neuroantigen" (NAg) refers to a type of autoimmune antigen that is a nervous system protein (central or peripheral) including an auto-reactive epitope. The neuroantigen can be a myelin basic protein (MBP), a proteolipid protein (PLP), myelin oligodendrocyte glycoprotein (MOG), myelin-associated oligodendrocytic basic protein (MOG), or other nervous system-derived proteins or a portion thereof and further including those derived from any species, and in particular, human, rat and mouse.

By the term "immunogenic" it is meant any substance or compound that stimulates an immune response.

By the term "tolerogen" it is meant any substance that stimulates immunological tolerance. By the terms "tolerogenic" or "tolerogenic activity" it is meant that a response of immunological tolerance is induced by an antigen or antigenic substance or an activity that results in the induction of immunological tolerance toward an antigen or antigenic substance.

The term "tolerance" as used herein refers to a decreased level of an immune response, a delay in the onset or progression of an immune response and/or a reduced risk of the onset or progression of an immune response. "Specific" immunological tolerance occurs when immunological tolerance is preferentially invoked against certain antigens in comparison with others. "Active" immunological tolerance refers to a state in which the tolerance effect(s) are the result of an ongoing biological process: for example, down-regulation of specific effector cells by suppressor cells. "Sustained tolerance" is tolerance that measurably persists for an extended period of time.

The terms "vaccination" or "immunization" are well-understood in the art. For example, the terms vaccination or immunization can be understood to be a process that increases a subject's immune reaction to antigen and therefore the ability to resist or overcome infection. In the case of the present invention, vaccination or immunization may decrease the recipient's immune response against self antigens thereby decreasing the likelihood of an autoimmune response.

"Polypeptide" as used herein, is used interchangeably with "protein," and refers to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

As used herein, a "functional" polypeptide is one that retains at least one biological, activity normally associated with that polypeptide. Preferably, a "functional" polypeptide retains all of the activities possessed by the native, unmodified or full-length peptide. By "retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits essentially no detectable biological activity normally associated with the polypeptide (e.g., at most, only an insignificant amount, e.g., less than about 10% or even 5%).

"Fusion protein" as used herein, refers to a protein produced when two heterologous nucleotide sequences or fragments thereof coding for two (or more) different polypeptides, or fragments thereof, are fused together in the correct translational reading frame. The two or more different polypeptides, or fragments thereof, include those not found fused together in nature and/or include naturally occurring mutants. One or more of the fusion proteins of the present invention can display at least some cytokine biological activity.

As used herein, a "fragment" or "portion" is one that substantially retains at least one biological activity normally associated with that protein or polypeptide. In particular embodiments, the "fragment" or "portion" substantially retains all of the activities possessed by the native or unmodified protein. By "substantially retains" biological activity, it is meant that the fragment or portion retains at least about 50%, 60%, 75%, 85%, 90%, 95%, 97%, 98%, 99%, or more, of the biological activity of the native protein (and can even have a higher level of activity than the native protein). In some embodiments, a fragment or portion of the protein or polypeptide described herein is at least 4, 6, 8, 10, 15, 20, 30, 50, 75, 100, 150, 200 or more contiguous amino acids and/or less than about 200, 150, 100, 75, 50, 30, 20, 15 or 10 contiguous amino acids, including any combination of the foregoing as long as the lower limit is less than the upper limit and induces an immune response.

A "recombinant" nucleic acid is one that has been created using genetic engineering techniques.

A "recombinant polypeptide" is one that is produced from a recombinant nucleic acid.

As used herein, an "isolated" nucleic acid (e.g., an "isolated DNA" or an "isolated vector genome") means a nucleic acid separated or substantially free from at least some of the other components of the naturally occurring organism or virus, such as for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide. As used herein, the "isolated" polypeptide is at least about 25%, 50%, 60%, 70%, 75%, 80%, 85%, 90%, 95%, 97%, 98%, 99% or more pure (w/w).

A "heterologous nucleotide sequence" will typically be a sequence that is not naturally-occurring in the vector. Alternatively, a heterologous nucleotide sequence can refer to a sequence that is placed into a non-naturally occurring environment (e.g., by association with a promoter with which it is not naturally associated; in a cell that does not contain an endogenous form of the heterologous nucleotide sequence and/or under the direction of a promoter and/or other regulatory elements with which it is not normally associate, in a cell that does contain an endogenous form of the heterologous nucleotide sequence).

There are no particular limits to the size of the heterologous nucleic acid. In particular embodiments, the heterologous nucleic acid is at least about 15, 18, 24, 50, 100, 250, 500, 1000, 1500, 2000, 3000, 4000 or more nucleotides long and/or less than about 4000, 3000, 2000, 1500, 1000, 500, 250 or 100 nucleotides long.

As used herein, a "vector" or "delivery vector" can be a viral or non-viral vector that is used to deliver a nucleic acid to a cell, tissue or subject. Exemplary vectors include, but are not limited to, adeno-associated virus vectors, adenovirus vectors, lentivirus vectors, paramyxovirus vectors, alphavirus vectors and herpes virus vectors.

A "recombinant" vector or delivery vector refers to a viral or non-viral vector that comprises one or more heterologous nucleotide sequences (i.e., transgenes), e.g., two, three, four, five or more heterologous nucleotide sequences. In an embodiment of the invention, the recombinant vectors and delivery vectors of the invention encode a fusion polypeptide of NAg and a cytokine such as IFN-β, but can also include one or more additional heterologous nucleotide sequences, for example, sequences encoding C- or N-terminal modifications and linker moieties.

As used herein, the term "viral vector" or "viral delivery vector" can refer to a virus particle that functions as a nucleic acid delivery vehicle, and which comprises the vector genome packaged within a virion. Alternatively, these terms can be used to refer to the vector genome when used as a nucleic acid delivery vehicle in the absence of the virion.

A viral "vector genome" refers to the viral genomic DNA or RNA, in either its naturally occurring or modified form. A "recombinant vector genome" is a viral genome (e.g., vDNA) that comprises one or more heterologous nucleotide sequence(s).

As used herein, the term "host cell" comprises prokaryotic cells and eukaryotic cells. Exemplary prokaryotic host cells include *E. coli, Bacillus subtilis*, etc. Exemplary eukaryotic cells include yeast cells, insect cells, mammal cells, etc.

2. ACTIVE AGENTS

Embodiments of the present invention provide the use of individual moieties that can be used together in a combination therapy. Embodiments of the present invention also provide the use of individual moieties that form a fusion protein that can then be used with other moieties as described herein to also provide a combination therapy. The individual moieties that can be used together comprise, consist essentially of or consists of an autoimmune antigen as described herein and an autoimmune cytokine. In particular, the autoimmune antigen can be a neuroantigen such as a nervous system protein including an auto-reactive epitope, as further example, an encephalitogenic determinant portion of a myelin protein.

The "anti-inflammatory" cytokine, which can also be referred to as an "immunoregulatory" cytokine is a naturally occurring or recombinant protein, analog thereof or fragment thereof that elicits an anti-inflammatory response in a cell that has a receptor for that cytokine. Cytokines of the present invention can include interleukin receptor antagonists from any species including murine and human such as IL-1-RA. Cytokines of the present invention can further include interleukins from any species including murine and human such as IL-1, IL-2, IL-3, IL-4, IL-5, IL-6, IL-7, IL-10, IL-12, IL-13, IL-14, IL-15, IL-16, IL-17 and IL-18, IL-19, IL-20, IL-21, IL-22, IL-23, IL-24, IL-25, IL-26, IL-27, IL-28A, IL-28B, IL-29, IL-31, IL-32, and IL-33, hematopoietic factors such as macrophage colony-stimulating factor (M-CSF), granulocyte-macrophage colony stimulating factor (GM-CSF), granulocyte colony stimulating factor (G-CSF) and erythropoietin, tumor necrosis factors (TNF) such as TNF-α and TGF-β, lymphokines such as lymphotoxin, regulators of metabolic processes such as leptin, interferons such as type I interferons, IFN-α, IFN-β, and IFN-γ and chemokines. In some embodiments of the invention, the anti-inflammatory cytokine is a type I interferon. In particular embodiments, the moieties include myelin basic protein (MBP) and IFN-β.

In some embodiments, the nervous system protein including an auto-reactive epitope is the encephalitogenic determinant portion of the myelin basic protein corresponding to (1) an amino acid sequence of SEQ ID NO:2, (2) an amino acid sequence having at least 80, 85, 90, 95 or 99% identity or homology with the amino acid sequence of SEQ ID NO:2, (3) an amino acid sequence encoded by a nucleic acid sequence encoding an encephalitogenic determinant portion of the myelin basic protein, or (4) an amino acid sequence encoded by a nucleic acid sequence that hydridizes with the complement of the nucleic acid sequence of (3) under stringent conditions as represented by hybridization conditions of 0.5M NaHPO$_4$, 7% sodium dodecyl sulfate (SDS), 1 mM EDTA at 65° C. and wash conditions of 0.1×SSC/0.1% SDS at 68° C.

The autoimmune antigen and the anti-inflammatory cytokine can be administered in conjunction, and as such, can be administered simultaneously or sequentially. The timing of administration can be such that the autoimmune antigen is administered before the anti-inflammatory cytokine, or the anti-inflammatory cytokine can be administered before the autoimmune antigen. Thus, in particular embodiments, MBP and IFN-β can be administered together either separately or as a mixture.

A fusion protein, according to embodiments of the present invention, comprises, consists essentially of or consists of (a) an autoimmune antigen, (b) an optional enterokinase linking moiety, and (c) an anti-inflammatory cytokine such as a type I interferon. In some embodiments, the autoimmune antigen is a neuroantigen such as myelin basic protein (MBP) or a portion thereof. In other embodiments, the neuroantigen is proteolipid protein (PLP), myelin oligodendrocyte glycoprotein (MOG), myelin-associated oligodendrocytic basic protein, or other nervous system-derived proteins or a portion thereof. In some embodiments, the neuroantigen includes an encephalitogenic determinant of the protein or a portion thereof. In other embodiments, the neuroantigen refers to the encephalitogenic determinant of the myelin basic protein as described above.

The enterokinase linking moiety is an amino acid sequence recognized by an enterokinase enzyme and can function as a linker between the autoimmune antigen domain and the anti-inflammatory cytokine domain of the fusion protein. The enterokinase linking moiety is (1) an amino acid sequence of SEQ ID NO:1, (2) an amino acid sequence having at least 80, 85, 90, 95 or 99% identity or homology with the amino acid sequence of SEQ ID NO:1, (3) an amino acid sequence encoded by a nucleic acid sequence encoding the enterokinase recognition site, or (4) an amino acid sequence encoded by a nucleic acid sequence that hydridizes with the complement of the nucleic acid sequence of (3) under stringent conditions as represented by hybridization conditions of 0.5M NaHPO$_4$, 7% sodium dodecyl sulfate (SDS), 1 mM EDTA at 65° C. and wash conditions of 0.1×SSC/0.1% SDS at 68° C.

When the anti-inflammatory cytokine in the fusion protein is a type I interferon, the type I interferon includes IFN-α, IFN-β, and IFN-γ as well as other type I interferons now known or to be determined.

Embodiments of the present invention further provide use of an isolated nucleic acid (e.g., an "isolated DNA" or an "isolated vector genome") that encodes the fusion protein described herein. The nucleic acid is separated or substantially free from at least some of the other components of the naturally occurring organism or virus, such as for example, the cell or viral structural components or other polypeptides or nucleic acids commonly found associated with the nucleic acid. The coding sequence for a polypeptide constituting the active agents of the present invention is transcribed, and optionally, translated. According to embodiments of the present invention, transcription and translation of the coding sequence will result in production of a fusion protein or individual polypeptides described. In some embodiments, the isolated nucleic acid encodes an autoimmune antigen as described herein and a cytokine to provide the fusion protein. In particular embodiments, the isolated nucleic acid encodes a fusion protein as described herein including the myelin basic protein or a portion thereof and IFN-β. The isolated nucleic acid may further encode an enterokinase recognition amino acid sequence.

It will be appreciated by those skilled in the art that there can be variability in the nucleic acids that encode the fusion polypeptides of the present invention due to the degeneracy of the genetic code. The degeneracy of the genetic code, which allows different nucleic acid sequences to code for the same polypeptide, is well known in the literature (see Table 1).

Further variation in the nucleic acid sequence can be introduced by the presence (or absence) of non-translated sequences, such as intronic sequences and 5' and 3' untranslated sequences.

Moreover, the isolated nucleic acids of the invention encompass those nucleic acids encoding fusion proteins that have at least about 60%, 70%, 80%, 90%, 95%, 97%, 98% or higher amino acid sequence similarity with the polypeptide sequences specifically disclosed herein or to those known sequences corresponding to proteins included in aspects of the present invention (or fragments thereof) and further encode functional fusion proteins as defined herein.

As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman (1981), *Adv. Appl. Math.* 2, 482; by the sequence identity alignment algorithm of Needleman & Wunsch (1970), *J. Mol. Biol.* 48, 443, by the search for similarity method of Pearson & Lipman (1988), *Proc. Natl. Acad. Sci. USA* 85, 2444, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984), *Nucl. Acid Res.* 12, 387-395, preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, (1987) *J. Mol. Eva* 35, 351-360; the method is similar to that described by Higgins & Sharp (1989), *CABIOS* 5, 151-153.

Another example of a useful algorithm is the BLAST algorithm, described in Altschul et al. (1990), *J. Mol. Biol.* 215, 403-410, and Karlin et al. (1993), *Proc. Natl. Acad. Sci. USA* 90, 5873-5787. A particularly useful BLAST program is the WU-BLAST-2 program which was obtained from Altschul et al. (1996), *Methods in Enzymology,* 266, 460-480; http://blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul et al., (1997) *Nucleic Acids Res.* 25, 3389-3402.

A percentage amino acid sequence identity value can be determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

To modify the amino acid sequences of the fusion proteins of the present invention, amino acid substitutions can be based on any characteristic known in the art, including the relative similarity or differences of the amino acid side-chain substituents, for example, their hydrophobicity, hydrophilicity, charge, size, and the like. In particular embodiments, substitutions (i.e., substitution with an amino acid residue having similar properties) are made in the amino acid sequence encoding a fusion protein or polypeptide used in the invention.

In making amino acid substitutions, the hydropathic index of amino acids can be considered. The importance of the hydropathic amino acid index in conferring interactive biologic function on a protein is generally understood in the art (see, Kyte and Doolittle (1982), *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Isolated nucleic acids of this invention include RNA, DNA (including cDNAs) and chimeras thereof. The isolated nucleic acids can further comprise modified nucleotides or nucleotide analogs.

The isolated nucleic acids encoding the polypeptides of the invention can be associated with appropriate expression control sequences, e.g., transcription/translation control signals and polyadenylation signals.

It will be appreciated that a variety of promoter/enhancer elements can be used depending on the level and tissue-specific expression desired. The promoter can be constitutive or inducible (e.g., the metalothionein promoter or a hormone inducible promoter), depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

The present invention further provides methods of making the fusion proteins described herein. Methods of making fusion proteins are well understood in the art. According to embodiments of the present invention, methods of making fusion proteins include those in accordance with U.S. Pat. Nos. 4,701,416; 5,496,924; 5,521,288; 5,837,816; 5,981,221; 5,994,104; 6,109,885; 6,211,342; 6,211,427; 6,369,199; 6,482,409; 6,555,342; 6,972,322; 6,987,006 7,087,411 and 7,112,659 and WO 2008/130382, which are incorporated herein by reference in their entirety. Such methods include growing a host cell including a vector that includes nucleic acids encoding the fusion protein under conditions appropriate for expression and subsequent isolation of the fusion protein. Accordingly, the isolated nucleic acids encoding a polypeptide constituting the fusion protein of the invention can be incorporated into a vector, e.g., for the purposes of cloning or other laboratory manipulations, recombinant protein production, or gene delivery. Exemplary vectors include bacterial artificial chromosomes, cosmids, yeast artificial chromosomes, phage, plasmids, lipid vectors and viral vectors (described in more detail below).

In particular embodiments, the isolated nucleic acid is incorporated into an expression vector. In further embodiments of the present invention, the vector including the isolated nucleic acids described herein is included in a host cell. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a polypeptide of the invention or active fragment thereof operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells or mammalian cells. Some suitable host cells are discussed further in Goeddel, *Gene Expression Technology*: Methods in Enzymology 185, Academic Press, San Diego, Calif. (1990). Examples of vectors for expression in yeast *S. cerevisiae* include pYepSecl (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen™, San Diego, Calif.). Baculovirus vectors available for expression of nucleic acids to produce proteins in cultured insect cells (e.g., Sf 9 cells) include the Bac-to-Bac® Baculovirus Expression System from Invitrogen.

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed above, the recombinant expression vector can contain additional nucleotide sequences. For example, the recombinant expression vector can encode a selectable marker gene to identify host cells that have incorporated the vector and/or may comprise another heterologous sequence of interest.

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

3. FORMULATIONS AND ADMINISTRATION

In terms of administration, the most suitable route in any given case will depend on the nature and severity of the condition being treated and on the combination of components, fusion protein, composition, viral vector, nucleic acid, or pharmaceutical formulation being administered.

The compositions described herein, fusion proteins, viral vectors and nucleic acids (e.g., DNA and/or RNA) of the invention can be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the fusion protein, composition described herein, viral vector or nucleic acid is typically admixed with, inter alia, an acceptable carrier. The carrier can be a solid or a liquid, or both, and is optionally formulated as a unit-dose formulation, which can be prepared by any of the well-known techniques of pharmacy.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like.

In the case of a solution, it can be lyophilized to a powder and then reconstituted immediately prior to use. For dispersions and suspensions, appropriate carriers and additives include aqueous gums, celluloses, silicates or oils.

For injection, the carrier is typically a liquid, such as sterile pyrogen-free water, pyrogen-free phosphate-buffered saline solution, bacteriostatic water, or Cremophor EL[R] (BASF, Parsippany, N.J.), parenterally acceptable oil including polyethylene glycol, polyvinyl pyrrolidone, lecithin, arachis oil or sesame oil, with other additives for aiding solubility or preservation may also be included. For other methods of administration, the carrier can be either solid or liquid.

For oral administration, the composition, fusion protein, viral vector or nucleic acid can be administered in solid dosage forms, such as capsules, tablets, and powders, or in liquid dosage forms, such as elixirs, syrups, and suspensions. The composition, fusion protein, viral vector or nucleic acid can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges including the fusion protein, compositions, viral vector or nucleic acid in a flavored base, usually sucrose and acacia or tragacanth; and pastilles including the fusion protein, compositions, viral vector or nucleic acid in an inert base such as gelatin and glycerin or sucrose and acacia.

Formulations of the present invention suitable for parenteral administration can include sterile aqueous and non-aqueous injection solutions of the fusion protein, compositions, viral vector or nucleic acid, which preparations are generally isotonic with the blood of the intended recipient. These preparations can contain anti-oxidants, buffers, bacteriostats and solutes, which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets. For example, in one aspect of the present invention, there is provided an injectable, stable, sterile composition including a composition, fusion protein, viral vector or nucleic acid of the invention, in a unit dosage form in a sealed container. Optionally, the active agents are provided in the form of a lyophilizate, which is capable of being reconstituted with a suitable pharmaceutically acceptable carrier to form a liquid composition suitable for injection thereof into a subject.

Formulations suitable for rectal or vaginal administration can be presented as suppositories. These can be prepared by admixing the composition, fusion protein, viral vector or nucleic acid with one or more conventional excipients or carriers, for example, cocoa butter, polyethylene glycol or a suppository wax, which are solid at room temperature, but liquid at body temperature and therefore melt in the rectum or vaginal cavity and release the composition, fusion protein, viral vector or nucleic acid.

Formulations suitable for topical application to the skin can take the form of an ointment, cream, lotion, paste, gel, spray, aerosol, or oil. Carriers that can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution. Suitable formulations comprise citrate or bis\tris buffer (pH 6) or ethanol/water.

The composition, fusion protein, viral vector or nucleic acid described herein can be formulated for nasal administration or otherwise administered to the lungs of a subject by any suitable means, for example, by an aerosol suspension of respirable particles including the composition, fusion protein, viral vector or nucleic acid, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles including the composition, fusion protein, viral vector or nucleic acid can likewise be produced with any solid particulate medicament aerosol generator, by techniques known in the pharmaceutical art.

Alternatively, one can administer the composition, fusion protein, viral vector or nucleic acid in a local rather than systemic manner, for example, in a depot or sustained-release formulation.

In particular embodiments of the invention, administration is by subcutaneous or intradermal administration. Subcutaneous and intradermal administration can be by any method known in the art including, but not limited to, injection, gene gun, powderject device, bioject device, microenhancer array, microneedles, and scarification (i.e., abrading the surface and then applying a solution including the composition, fusion protein, viral vector or nucleic acid).

In other embodiments, the composition, fusion protein, viral vector or nucleic acid is administered intramuscularly, for example, by intramuscular injection or by local administration.

Nucleic acids (e.g., DNA and/or RNA) can also be delivered in association with liposomes, such as lecithin liposomes or other liposomes known in the art (for example, as described in WO 93/24640) and may further be associated with an adjuvant. Liposomes including cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. PCT publication WO 94/27435 describes compositions for genetic immunization including cationic lipids and polynucleotides. Agents that assist in the cellular uptake of nucleic acid, such as calcium ions, viral proteins and other transfection facilitating agents, may be included.

Polynucleotide immunogenic preparations may also be formulated as microcapsules, including biodegradable time-release particles. U.S. Pat. No. 5,151,264 describes a particulate carrier of phospholipid/glycolipid/polysaccharide nature that has been termed Bio Vecteurs Supra Moleculaires (BVSM).

In particular embodiments, the mode of administration is parenteral for the methods employing the use of the autoimmune antigen or portion thereof in combination with the autoimmune cytokine, each as described herein, where these moieties do not comprise a fusion protein. For example, the autoimmune antigen or the autoimmune cytokine or both can be administered parenterally. In particular embodiments, the mode of administration is parenteral administration of myelin basic protein or a portion thereof in combination with IFN-β.

Methods of the present invention further include administering an effective amount of the active agents of the present invention, as described above, to the subject. The effective amount of the active agent, the use of which is in the scope of the present invention, will vary somewhat from subject to subject, and will depend upon factors such as the age and condition of the subject and the route of delivery. Such dosages can be determined in accordance with routine pharmacological procedures known to those skilled in the art. For example, the active agents of the present invention can be administered to the subject in an amount ranging from a lower limit from about 0.01, 0.05, 0.10, 0.50, 1.0, 5.0, or 10% to an upper limit ranging from about 10, 20, 30, 40, 50, 60, 70, 80, 90, 95, 96, 97, 98, 99, or 100% by weight of the composition. In some embodiments, the active agents include from about 0.05 to about 95% by weight of the composition. In other embodiments, the active agents include from about 0.05 to about 60% by weight of the composition. In still other embodiments, the active agents include from about 0.05 to about 10% by weight of the composition.

In particular embodiments of the present invention, the composition described herein is immunogenic, and the administration of the active agents can be carried out therapeutically (i.e., as a rescue treatment) or prophylactically. For example, in some embodiments, to protect against an autoimmune disease, subjects may be vaccinated in anticipation of antigen exposure, as neonates or adolescents. Subjects who have not previously been exposed to the disease may also be vaccinated. Moreover, subjects afflicted with an autoimmune disease may be administered the immunogenic composition during a period of remission in order to prevent a relapse of the disease. The immunogenic composition of the present invention can be given as a single dose schedule or in a multiple dose schedule. A multiple dose schedule is one in which a primary course of administration may consist of about 1 to 10 separate doses, followed by other doses (i.e., booster doses) given at subsequent time intervals to maintain and/or reinforce the immune response, for example, at about 1 to 4 months for a second dose, and if needed, a subsequent dose(s) after another several months. The dosage regimen will also, at least in part, be determined by the need of the individual and be dependent upon the judgment of the medical or veterinary practitioner.

Embodiments of the present further provide kits comprising one or more containers having pharmaceutical dosage units including an effective amount of the compositions and/or components of the compositions described herein, wherein the container is packaged with optional instructions for the use thereof.

As described in further detail below, the present invention finds use in both veterinary, medical and research applications. Suitable subjects include avians, mammals and fish, with mammals being preferred. The term "avian" as used herein includes, but is not limited to, chickens, ducks, geese, quail, turkeys and pheasants. The term "mammal" as used herein includes, but is not limited to, primates (e.g., simians and humans), bovines, ovines, caprines, porcines, equines, felines, canines, lagomorphs, rodents (e.g., rats and mice), etc. Human subjects include fetal, neonatal, infant, juvenile and adult subjects.

4. METHODS OF USE

Embodiments of the present invention provide methods of regulating an immunological disorder including administering an effective amount of (i) an autoimmune antigen or portion thereof in conjunction with (ii) an anti-inflammatory cytokine, with the proviso that (i) and (ii) do not comprise a fusion protein.

Embodiments of the present invention also provide methods of regulating an immunological disorder comprising administering to a subject an effective amount of a fusion protein as described herein or a composition described herein.

According to embodiments of the present invention, the immunological disorder includes autoimmune diseases, allergic or hypersensitivity diseases, transplant rejection and tissue disorders.

Autoimmune diseases include, but are not limited to, those affecting biological systems such as the circulatory system, digestive system, endocrine system, integumentary system, lymphatic system, muscular system, nervous system, reproductive system, respiratory system, skeletal system or urinary system. In particular, the biological systems can include the Nervous system: Acute disseminated encephalomyelitis (demyelinating inflammation following vaccination or infection); Myasthenia Gravis (anti-AchR antibodies, blockade of neuromuscular junction); Multiple sclerosis (inflammation of CNS myelin); Acute inflammatory demyelinating polyneuropathy/Guillain-Barre syndrome (inflammation of peripheral myelin); Endocrine system: Hashimoto's Thyroiditis (anti-thyroid antibodies, hypothyroidism); Grave's Disease (auto-antibodies stimulate TSH receptors on thyroid follicular cells, hyperthyroidism); Insulin-Dependent Diabetes Mellitus (i.e. juvenile diabetes, inflammation and deletion of β islet cells); Autoimmune adrenal insufficiency (e.g. Addison's disease, inflammation coupled with progressive scarring and atrophy of adrenal glands); Autoimmune oophoritis (inflammation of ovaries, infertility); Autoimmune orchitis (inflammation of testis); Hematopoietic system: Autoimmune hemolytic anemia (anti-erythrocyte antibodies); Paroxysmal cold hemoglobinuria (mediated by IgM cold agglutinins against erythrocytes); Idiopathic thrombocytopenic purpura (anti-platelet antibodies, bleeding); Autoimmune neutropenia (antibodies against neutrophils cause degranulation, neutrophil depletion, and vasculitis); Pernicious anemia (progressive destruction of gastric fundic gland, loss of intrinsic factor, and malabsorption of vitamin $B_{12}$); Autoimmune coagulopathy (circulating anti-coagulants, anti-phospholipid antibody syndrome, neutralizes phospholipids necessary for clotting activity); Gastrointestinal Tract: Primary biliary cirrhosis (intrahepatic bile duct and portal inflammation leading to fibrosis and cirrhosis); Inflammatory bowel disease (Crohn's disease, ulcerative colitis); Kidney: Glomerulonephritis (antibody against glomerular basement membrane); Immune complex glomerular nephritis (accumulation of deposited immune complexes in basement membrane); Skin: *Pemphigus vulgaris* (loss of adhesion between epidermal cells, blistering, antibody against stratified squamous epithelium);

Systemic autoimmune disease: Systemic Lupus Erythematosus (arthralgias, rash, nephritis, anti-nuclear antibodies); Rheumatoid Arthritis (inflammatory polyarticular arthritis, rheumatoid factor); Sjogren's syndrome (inflammation of lacrymal and parotid glands with arthritis); Polymyositis (inflammation of skeletal muscle); Dermatomyositis (inflammation of skin and skeletal muscle); Scleroderma (progressive systemic sclerosis, sclerosis of skin and internal organs); and Cardiac and vascular diseases: Autoimmune myocarditis (inflammation of cardiac muscle); Immune complex-mediated vasculitis (passive deposition of immune complexes in vessel walls followed by C-mediated lysis and inflammation); Polyarteritis nodosa (type of necrotizing vasculitis that follows certain types of infections). In some embodiments of the present invention, the autoimmune disease is an autoimmune disease affecting the nervous system, endocrine system, hematopoietic system, gastrointestinal tract, renal system, cardiac system, vascular system, musculoskeletal system or a combination thereof. In some embodiments, the autoimmune disease is a systemic autoimmune disease. In particular embodiments, the autoimmune disease is multiple sclerosis.

Allergic or hypersensitivity diseases include, but are not limited to, allergic rhinitis, asthma, atopic dermatitis, allergic gastroenteropathy, contact dermatitis, drug allergy or a combination thereof. In particular embodiments, the present invention provides active agents, compositions and methods to induce antigen-specific immunological tolerance to allergens responsible for the allergic diseases described, herein.

Transplant rejection and tissue disorders include, but are not limited to, those affecting the kidney, liver, pancreas, heart, lung, bone, skin and combinations thereof. In particular embodiments, the present invention provides compositions and methods to induce antigen-specific immunological tolerance to allogeneic and xenogeneic transplantation antigens that may contribute to the rejection of tissue transplants, and thus, facilitate acceptance of kidney transplants, liver transplants, pancreas transplants, skin grafts, heart transplants, and heart-lung transplant. The active agents and methods may also alleviate complications of bone marrow transplantation (i.e., graft versus host disease).

It is contemplated that diseases and/or disorders treated by the methods of this invention can include any disease or disorder that can be treated by mounting an effective tolerogenic response to a fusion protein or composition of the invention. Accordingly, embodiments of the present invention provide methods of modulating an immune response including administering a fusion protein or composition as described herein in an amount sufficient to elicit a tolerogenic response. In some embodiments, the immune response is antigen-specific. In some embodiments, the administering step is carried out in vivo or ex vivo. In still other embodiments, the tolerogenic response is an active tolerance mechanism. In particular embodiments, the tolerogenic response is a sustained tolerogenic response.

It is also contemplated that the fusion proteins and compositions of this invention can be used as a vaccine or prophylactic composition and further employed in methods of preventing a disease or disorder in a subject, comprising administering to the subject an effective amount of an active agent of this invention. The vaccine or prophylactic composition can be administered to a subject who is identified to be at risk of contracting a particular disease or developing a particular disorder and in whom the ability to elicit an immune response to an antigen may be impaired. Identification of a subject at risk can include, for example, evaluation of such factors as family history, genetic predisposition, age, environmental exposure, occupation, lifestyle and the like, as are well known in the art.

The effective dosage of any specific active agent will vary somewhat from composition to composition, patient to patient, and will depend upon the condition of the patient and the route of delivery. As a general proposition, a dosage from about 0.1 to about 50 mg/kg will have therapeutic efficacy, with still higher dosages potentially being employed for oral administration, wherein aerosol administration is usually lower than oral or intravenous administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

In particular embodiments, administration to a subject such as a human, a dosage of from about 0.01, 0.1, or 1 mg/kg up to 50, 100, or 150 mg/kg or more for each active agent can be employed. Depending on the solubility of the particular formulation of active agents administered, the daily dose can be divided among one or several unit dose administrations.

Having now described the invention, the same will be illustrated with reference to certain examples, which are included herein for illustration purposes only, and which are not intended to be limiting of the invention.

EXAMPLES

Example 1

Methods of Making Exemplary Fusion Proteins

Recombinant Protein Structure.

The IFNβ-NAg fusion protein was expressed by use of a recombinant baculovirus system. The recombinant baculovirus technology was described previously (Mannie, M. D., J. L. Devine, B. A. Clayson, L. T. Lewis, and D. J. Abbott. 2007c. Cytokine-neuroantigen fusion proteins: new tools for modulation of myelin basic protein (MBP)-specific T cell responses in experimental autoimmune encephalomyelitis. *J Immunol Methods* 319:118-132 and WO/2008130382). The IFNβ-NAg fusion protein included the order from the N-terminus to C-terminus as shown in Table 2. Rat IFNβ cytokine was the N-terminal domain (NM_019127) which was fused by a G-D-D-D-D-K-G (SEQ ID NO. 1) enterokinase (EK) linker to the dominant 73-87 encephalitogenic epitope (P-Q-K-S-Q-R-S-Q-D-E-N-P-V-V-H) (SEQ ID NO. 2) of guinea pig myelin basic protein (GPMBP, accession P25188) followed by five additional H residues to form a C-terminal 6-histidine tag. Both the cytokine and NAg domains had full biological activity. The amino acid sequence of human myelin basic protein (full length; accession number CAA35179) is as follows: MASQKRPSQRHGSKYLATASTMDHARHGFLPRHRDTGILDSIGRFFGGDRGAP KRGSGKVPWLKPGRSPLPSHARSQPGLCNMYKDSHHPARTAHYGSLPQKSHG RTQDENPWHFFKNIVTPRTPPPSQGKGRGLSLSRFSWGAEGQRPGFGYGGR ASDYKSAHKGFKGVDAQGTLSKIFKLGGRDSRSGSPMARR (SEQ ID NO. 3). The sequence YGSLPQKSHGRTQDENPWHF (SEQ ID NO. 4) represents the sequence that is homologous to the rat encephalitogenic sequence.

The native IFNβ signal sequence directed secretion of the fusion protein as a biologically active protein into the supernatant of baculovirus-infected Sf9 cells. The IFNβ-NAg fusion gene and five additional IFNβ-based fusion genes were cloned in pVAX1 and pCEP4 expression plasmids (Invitrogen) and were expressed by transient transfection of human embryonic kidney cells (HEK293) cells (Table 2). The genes for these fusion proteins were assembled by overlap extension PCR, and the resulting fusion genes were inserted into the expression plasmid by directional, restriction endonuclease-free, whole plasmid PCR. The inserts were subjected to forward and reverse DNA sequencing to verify the predicted DNA sequence.

Purification of Fusion Proteins.

Expression supernatants were concentrated on YM10 ultrafiltration membranes and were subjected to consecutive affinity chromatography steps (Mannie et al. 2007). The first affinity chromatography step was based on the use of a single chain Fv anti-6his antibody fused to two tandem chitin-binding domains (scFv-CBD2) (Blank, K., P. Lindner, B. Diefenbach, and A. Pluckthun. 2002. Self-immobilizing recombinant antibody fragments for immunoaffinity chromatography: generic, parallel, and scalable protein purification. *Protein Expr Purif* 24:313-322.28). This recombinant protein was immobilized on a chitin resin column by stable binding of the tandem chitin binding domains to the chitin bead resin. Immobilization of the scFv anti-6his single chain antibody onto chitin columns enabled purification of recombinant proteins bearing C-terminal 6-histidine tags from concentrated baculovirus supernatants. These columns were maintained in TBST buffer (50 mM Tris-HCl, 500 mM NaCl, 0.1 mM EDTA, 1% Triton X-100, 0.01% Na azide, pH 8.0). Before each use, columns were equilibrated in MBS buffer (20 mM MES, 500 mM NaCl, 0.1 mM EDTA, pH 6.5), and concentrated expression supernatants were passed through the column to trap the 6his-tagged protein. The fusion proteins were eluted in CAPS buffer (50 mM CAPS, 500 mM NaCl, 0.1 mM EDTA, pH 10.0), were concentrated, and were directly applied to Ni-NTA Agarose columns (Qiagen) followed by extensive washing of the resin (50 mM $NaH_2PO_4$, 500 mM NaCl, 10 mM imidazole, pH 8.0). IFNβ-NAg or IFNβ was eluted by acid elution (pH 4.5) and was concentrated and diafiltrated in Amicon Ultra-15 centrifugal filter devices. Protein quantity was assessed by the BCA protein assay (Pierce) and by absorbance at 280 nm. Purity was assessed by SDS-PAGE.

Animals and Reagents.

A colony of Lewis rats was maintained at East Carolina University School of Medicine. Animal care and use was approved by the Institutional Animal Care and Use Committee and was performed in accordance with approved institutional guidelines. The synthetic peptide gp69-88 (YG-SLPQKSQRSQDENPWHF) (SEQ ID NO. 5) was obtained from Quality Controlled Biologicals, Inc. (Hopkinton, Mass.). The purity of gp69-88 was greater than 98%. The peptide was freely soluble and was routinely reconstituted in saline. The OX6 anti-I-A (RT1B) IgG1, the R73 anti-TCRβ IgG1, the OX81 anti-IL-4 IgG1, and the OX18 anti-MHC class I glycoproteins (MHC-I) (RT1A) IgG1 were concentrated by ultrafiltration of B cell hybridoma supernatants through Millipore spiral wound membranes (100 kd exclusion). Hybridomas were obtained from the European Collection of Cell Cultures. The B5 IgM anti-MHC-I ($RT1A^{a,b,l}$) mAb was purchased from BD Biosciences. FITC-conjugated goat anti-mouse IgG1 was purchased from Southern Biotechnology (Birmingham, Ala.).

Cell Lines and Culture Conditions.

The RsL.11 MBP-specific clone was a stable, IL-2 dependent line derived from Lewis rats sensitized with rat MBP in CFA (Mannie, M. D., and M. S. Norris. 2001. MHC class-II-restricted antigen presentation by myelin basic protein-specific CD4+ T cells causes prolonged desensitization and outgrowth of CD4- responders. *Cell Immunol* 212:51-62). The RsL.11T clone was a transformed variant of the RsL.11 clone. The R1T T cell clone (also referred to as R1-trans) was a transformed, IL-2 dependent clone derived from Lewis rats that constitutively expressed MHC class II glycoproteins (MHC-II), B7.1, and B7.2 (Mannie et al. 2001; Patel, D. M., P. Y. Arnold, G. A. White, J. P. Nardella, and M. D. Mannie. 1999. Class II MHC/peptide complexes are released from APC and are acquired by T cell responders during specific antigen recognition. *J Immunol* 163:5201-5210). The BN-GP T cell line was a transformed variant of a IL-2 dependent, MBP-specific clone derived from Brown Norway rats (Patel et al. 1999; Mannie, M. D., J. G. Dawkins, M. R. Walker, B. A. Clayson, and D. M. Patel. 2004. MHC class II biosynthesis by activated rat CD4+ T cells: development of repression in vitro and modulation by APC-derived signals. *Cell Immunol* 230:33-43). These lines originated as primary T cell lines that exhibited a quiescent resting phase during long-term maintenance in IL-2 but spontaneously transformed to a constitutive blastogenic, proliferative phenotype. These variant T cell lines were IL-2 dependent and did not revert to a resting phase during maintenance culture in IL-2. The Conal.8D9 clone was isolated from Lewis rats and was specific for conalbumin (Sigma) (Mannie, M. D., J. P. Nardella, G. A. White, P. Y. Arnold, and D. K. Davidian. 1998. Class II MHC/peptide complexes on T cell antigen-presenting cells: agonistic antigen recognition inhibits subsequent antigen presentation. *Cell Immunol* 186.111-120; Mannie, M. D., G. A. White, J. P. Nardella, D. K. Davidian, and P. Y. Arnold. 1998. Partial agonism elicits an enduring phase of T-cell-medicated antigen presentation. *Cell Immunol* 186:83-93). CTLL T cells represented an IL-2 dependent line of murine T cells (Gillis, S., and K. A. Smith. 1977. Long term culture of tumour-specific cytotoxic T cells. *Nature* 268:154-15634). Assays were performed in complete RPMI medium [10% heat-inactivated fetal bovine serum, 2 mM glutamine, 100 ug/ml streptomycin, 100 U/ml penicillin (Whittaker Bioproducts, Walkersville, Md.), 50 uM 2-ME (Sigma)]. T cell lines were propagated in complete RPMI supplemented with recombinant rat IL-2 (0.4% v/v Sf9 supernatant) (Mannie, M. D., D. J. Fraser, and T. J. McConnell. 2003. IL-4 responsive CD4+ T cells specific for myelin basic protein: IL-2 confers a prolonged postactivation refractory phase. *Immunol Cell Biol* 81:8-1935).

Measurement of Antigen-Specific Proliferation and IL-2 Production.

Cultures were pulsed with 1 uCi of [$^3$H]thymidine (6.7 Ci/mmol, New England Nuclear) during the last day of a 3 or 4 day culture. Cultures were harvested onto filters by use of a Tomtec Mach III harvester. [$^3$H]thymidine incorporation into DNA was measured by use of a Wallac 1450 Microbeta Plus liquid scintillation counter. Error bars represent standard deviations of triplicate or quadruplet sets of wells.

Flow Cytometric Analysis.

T cells were incubated with a 1/20 titration of a concentrated supernatant containing the designated mAb for 45 minutes at 4° C. The cells were washed two times and were incubated for 45 minutes with a FITC-conjugated secondary reagent. Dead cells were excluded from analysis by forward versus side scatter profiles. Data were acquired with a Becton Dickinson FACScan flow cytometer and were analyzed with the CELLQuest software program.

Induction of EAE, Tolerance Induction, and Clinical Assessment of EAE.

EAE was induced in Lewis rats by injection of an emulsion containing 50 ug of dihydrofolate reductase (DHFR)-NAg (Mannie et al. 2007a; Mannie et al. 2007b) in CFA (200 µg *Mycobacterium tuberculosis*) in a total volume of 0.1 ml. DHFR-NAg was comprised of the mouse dihydrofolate reductase as the N-terminal domain and the encephalitogenic GP69-87 peptide of GPMBP as the C-terminal domain. The DHFR-NAg fusion protein was equivalent to gp69-88 for induction of EAE (data not shown). The emulsion was injected subcutaneously in two 0.05 ml volumes on either side of the base of the tail. To determine whether IFNβ-NAg prevented active induction of EAE, rats were given injections of 1 nmole IFNβ-NAg in saline on days −21, −14, and −7, and then seven days after the last injection, rats were challenged with DHFR-NAg in CFA (day 0) to induce EAE. Alternatively, rats were challenged with DHFR-NAg in CFA and then were treated with IFNβ-NAg or control reagents on day 9 (1 nmole), day 10 (1 nmole), and day 12 (0.5 nmole) or as otherwise designated. The following scale was used to score EAE: paralysis in the distal tail, 0.25; limp tail, 0.5; ataxia, 1.0; hind leg paresis, 2.0; full hind leg paralysis, 3.0. Ataxia was scored as an uneven or wobbly gait. Hind leg paresis was scored as the retention of some voluntary ambulatory movement in the hind-limbs but without the ability to ambulate upright.

Statistical Analysis.

Mean cumulative score, mean maximal score, and the mean number of days with severe EAE were analyzed by parametric ANOVA. The mean cumulative score was calculated by summing the daily scores for each rat and then averaging the cumulative scores to obtain the mean cumulative score for the group. The mean maximal score was calculated by averaging the most severe score of EAE for all rats in each group. Means were reported together with the standard deviation. Median cumulative score and median maximal score were listed as the median values for all rats in each group and were analyzed by nonparametric ANOVA based on ranked data. ANOVA was interpreted with the Bonferroni Post-Hoc Test. One-way ANOVA was used to assess data from a single experiment, whereas two-way ANOVA (variable versus experiment) was used to assess data compiled from two separate experiments. "Incidence of severe EAE" was analyzed pair-wise with the Fisher's Exact Test. Severe EAE was defined as the incidence of hind-leg paresis (EP; 2.0) or full hindlimb paralysis (P; 3.0) (Tables 3-6), unless designated otherwise (Table 7).

Example 2

Biological Activity

Biological Activity of the Cytokine Domain.

Figure 2:
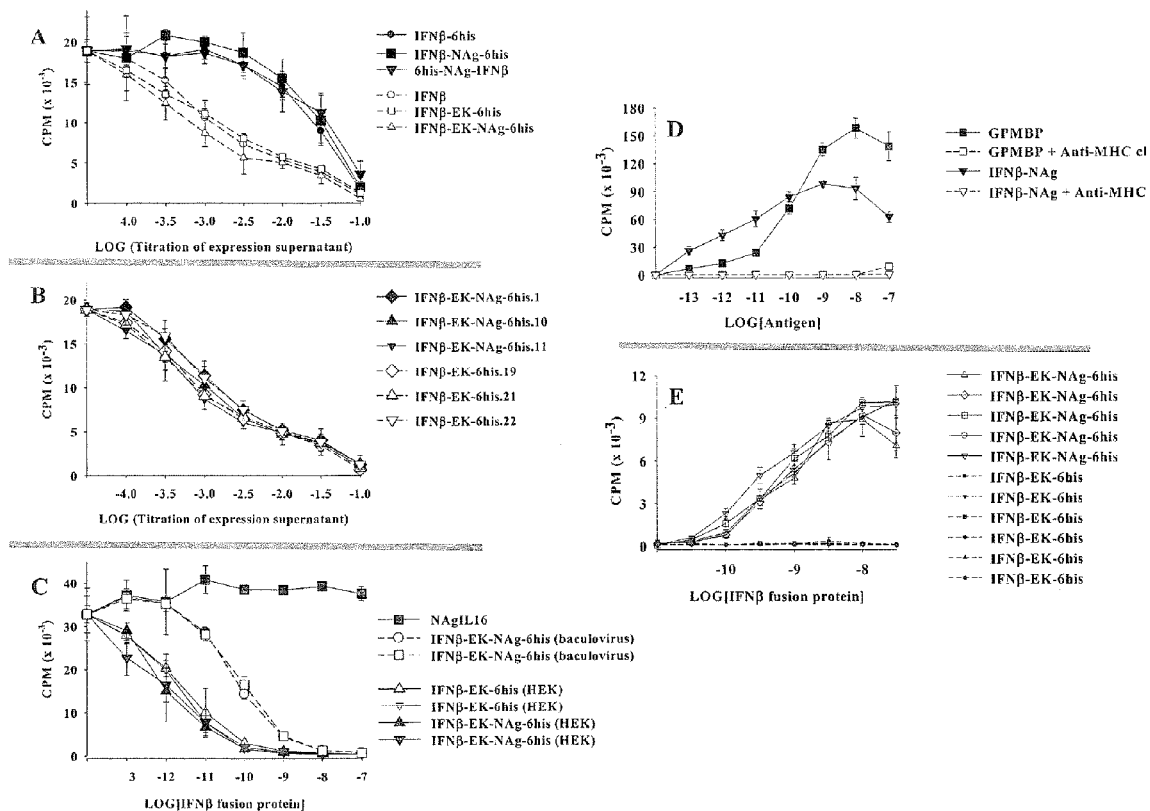
FIG. 2. Structure-function analysis of the cytokine and NAg domains of IFNβ fusion proteins. (A) Expression supernatants containing designated IFNβ fusion proteins (see Table 2) were added to cultures of BN-GP T cells at designated titrations (x-axis). (B) The IFNβ-EK-NAg-6his or IFNβ-EK-6his fusion genes were inserted into the pCEP4 expression vector (Invitrogen). Inserts were verified by DNA sequencing, and the genes were expressed by transient transfection of HEK293 cells. Independently derived expression systems of IFNβ-EK-NAg-6his or IFNβ-EK-6his (3 each) were compared in the BN-GP T cell anti-proliferative assay. (C) Independently purified preparations (2 each) of each IFN-β fusion protein (IFNβ-NAg from HEK293 cells, IFNβ-NAg from baculovirus, and IFN-β from HEK293 cells) were added at designated concentrations to assess anti-proliferative activity. Two independently purified preparations of the same fusion protein were tested to verify the reliability of activity for each type of protein. The x-axis was based on the exponent of the molar concentration. For example, a concentration of 100 nM was represented as Log [10$^{-7}$]=Log$_{10}$ (10$^{-7}$M)=−7 and was plotted by the exponent of −7. For these experiments (A-C), BN-GP T cells were cultured in IL-2. (D) The MBP-specific RsL.11 T cell clone and irradiated splenic APC were cultured with designated concentrations of purified IFNβ-NAg or GPMBP in the presence or absence of the OX6 anti-MHC-II mAb. (E) Five preparations of purified IFNβ-NAg and six preparations of purified IFN-β were tested for antigenic activity in cultures of RsL.11 T cells and irradiated splenic APC. These data are representative of at least three independent experiments.

The main objective of the study was to test IFNβ as a fusion partner for generation of tolerogenic cytokine-NAg vaccines. The initial question was whether the cytokine and NAg domains of an IFNβ-NAg fusion protein were biologically active. IFNβ-NAg fusion proteins and relevant controls were expressed in baculovirus and by transient transfection of HEK293 cells. The biological activity of the IFNβ domain of the fusion protein was assessed by assays measuring IFNβ-mediated induction of MHC-I and anti-proliferative activity (FIGS. 1, 2A, 2B, 2C). The activity of the NAg domain was measured in NAg-specific T cell proliferation assays (FIGS. 2D & 2E). The IFNβ-NAg fusion protein was comprised of rat IFNβ as the N-terminal domain and a C-terminal domain containing an EK linker, the NAg domain (the encephalitogenic 73-87 epitope of myelin basic protein), and a C-terminal 6-histidine sequence (Table 2). This fusion protein had a predicted MW of 22,922 daltons with 4 potential N-linked glycosylation sites.

Two identical baculovirus expression systems of IFNβ-NAg were independently derived (IFNβ-NAg.1 and IFNβ-NAg.4) to test biological activities of the cytokine and NAg domains. To measure the ability of IFNβ-NAg to induce MHC-I, thymocytes were cultured with or without a 1% titration of a baculovirus expression supernatant containing the IFNβ-NAg.1 fusion protein. After 2 days of culture, the thymocytes were analyzed by flow cytometry for expression of MHC-I. Supernatants containing the IFNβ-NAg.1 (FIG. 1A, top panels) or IFNβ-NAg.4 (not shown) induced the expression of MHC-I on immature thymocytes. Mock baculovirus supernatants lacked activity (FIG. 1A, bottom). Although the IFNβ domain of IFNβ-NAg augmented MHC-I expression, this domain did not affect TCRβ expression (FIG. 1A) or other markers such as CD4, Thy1.1, LFA-1, MHC-II, CD2, CD5, CD28, CD45, or CD48 (not shown). These data indicated that the IFNβ domain of the IFNβ-NAg fusion protein was biologically active.

Baculovirus expression supernatants containing the IFNβ-NAg fusion protein also efficiently caused death of the BN-GP T cell line (FIG. 1B). Expression supernatants containing IFNβ-NAg inhibited the IL-2 dependent proliferation of BN-GP T cells by induction of cell stasis followed by extensive cell death (not shown). Both IFNβ-NAg fusion proteins were active at titrations of $10^{-4}$ whereas baculovirus supernatants containing other cytokine-NAg fusion proteins including IL1RA-NAg, IL2-NAg, IL4-NAg, IL10-NAg, IL13-NAg, and NAg-IL16 as well as mock baculovirus supernatants had no activity. These control cytokine-NAg fusion proteins were active in bioassays specific for the respective cytokine domains (Mannie et al. 2007b; Mannie et al. 2007c). IFNβ-NAg caused cell death independently of the NAg domain, because BN-GP T cells did not recognize the 73-87 peptide sequence of MBP (not shown). IFNβ-NAg also directly caused the death of other IL-2 dependent T cells lines, including the NAg-specific RsL.11 clone as well as a transformed variant of the RsL.11 clone (RsL.11T) and a conalbumin-specific clone (Conal.8D9) (FIG. 1C). IFNβ-NAg mediated killing of RsL.11 T cells was dependent upon the cytokine domain where killing was not blocked by anti-MHC-II mAb (not shown). IFNβ-NAg did not kill a transformed variant of another NAg-specific clone (R1T). These data indicated that IFNβ was able to kill certain rat T cell lines but not others. IFNβ-NAg did not kill murine CTLL T cells even though rat IFNβ is able to efficiently kill mouse T cells (not shown). These data show that the IFNβ-NAg fusion protein had high levels of IFNβ-specific biological activity.

The C-terminal 6-histidine sequence of the IFNβ-NAg fusion was accessible and enabled affinity purification of the fusion protein from expression supernatants (FIG. 1D).

Optimization of Rat IFNβ Fusion Proteins.

The IFNβ-NAg fusion protein had the domain structure IFNβ-EK-NAg-6his (Table 2) and was successfully expressed in a baculovirus expression system. Control IFN-β protein in baculovirus that included an IFNβ-6his sequence was expressed inefficiently (not shown). To assess an optimal structure for IFNβ-NAg and a control IFN-β protein, six different fusion proteins were expressed by transient transfection of HEK293 cells (Table 2 and FIG.

2A). Optimal expression was achieved when the IFNβ protein did not have non-native C-terminal or N-terminal additions. Optimal expression was also observed in proteins that included an EK linker separating the N-terminal cytokine domain and the C-terminal domain. That is, expression of IFNβ, IFNβ-EK-6his, or IFNβ-EK-NAg-6his was optimal and resulted in essentially equal interferon activity. In contrast, fusion proteins lacking the EK linker such as IFNβ-6his or IFNβ-NAg-6his were not efficiently expressed. An additional fusion protein (6his-NAg-IFNβ) was also expressed in which the N-terminal IFNβ signal sequence was directly fused to a 6his-NAg domain, and the C-terminal domain included the mature IFN-β cytokine. This ordering of domains was successfully used to construct the NAg-IL16 fusion protein, but the 6his-NAg-IFNβ fusion protein was not efficiently expressed. In conclusion, an EK linker appeared to facilitate the efficient expression of biologically active, stable IFNβ fusion proteins.

The finding that IFN-β fused to either an EK-NAg-6his C-terminus or EK-6his C-terminus had equal cytokine activity (FIG. 2A) was reinforced by testing independently derived expression plasmids encoding IFNβ-EK-NAg-6his or IFNβ-EK-6his proteins (FIG. 2B). The two purified proteins (IFNβ-EK-NAg-6his vs IFNβ-EK-6his) also exhibited essentially equipotent cytokine activity (FIG. 2C). Both IFNβ fusion proteins exhibited half-maximal inhibition at concentrations in the 1-10 pM range. These potencies were equal or superior to those reported for commercial IFN preparations. IFNβ-EK-NAg-6his proteins purified from baculovirus expression supernatants however were less active. The amino acid sequences of the IFNβ-EK-NAg-6his protein expressed in the HEK and baculovirus systems were identical. The main structural correlates of this activity difference appeared to involve distinct patterns of glycosylation (not shown).

Biological Activity of the NAg Domain.

The activity of the NAg domain was confirmed by assaying antigen-specific proliferation of the myelin basic protein-specific RsL.11 T cell clone in the presence of splenic APC (FIG. 2D). The stimulatory activity of purified IFNβ-EK-NAg-6his (IFNβ-NAg) was completely inhibited by the OX6 anti-class II MHC mAb. These data indicated that the NAg peptide of the IFNβ-NAg was efficiently processed and presented by MHC-II to an antigen-specific T cell clone. The proliferative response was dependent upon the NAg domain. Five independently purified preparations of IFNβ-EK-NAg-6his exhibited similar stimulatory activity whereas six independently purified preparations of IFNβ-EK-6his were devoid of stimulatory activity (FIG. 2E). The IFNβ-EK-NAg-6his protein, at low concentrations, appeared more potent than intact guinea pig myelin basic protein (GPMBP) (FIG. 2D) or the synthetic gp69-88 peptide (not shown). These data provide evidence that the cytokine domain may facilitate presentation of the NAg by professional APC, as was described for the IL4-NAg, IL2-NAg, and NAg-IL16 fusion proteins (Mannie et al. 2007a; Mannie et al. 2007b and Mannie et al. 2007c). Although the antigenic potency of IFNβ-NAg appeared greater than GPMBP as measured by the concentration eliciting a half-maximal response, the peak proliferative response stimulated by IFNβ-NAg was substantially less than that stimulated by GPMBP. The latter observation may reflect the cytotoxic or anti-proliferative activity of the IFNβ domain in this concentration range.

IFNβ-NAg Fusion Proteins Prevented EAE.

Figure 3:
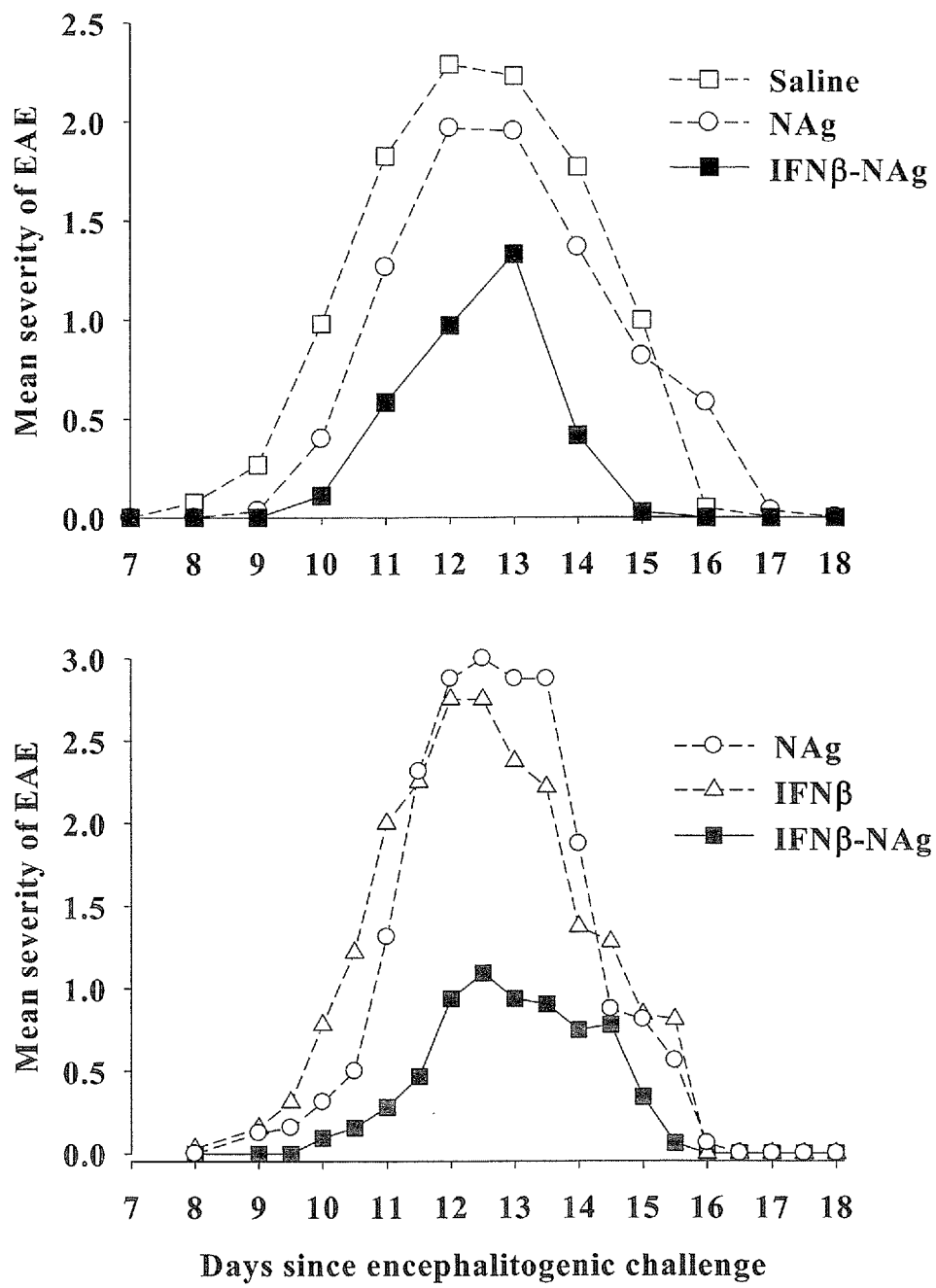
FIG. 3. The IFNβ-NAg fusion protein prevented the subsequent induction of EAE whereas neither IFNβ nor NAg alone had tolerogenic activity. Shown are disease time-courses for experiments shown in Table 3 (A) and pooled data from experiments 1 and 2 of Table 4 (B). Rats were treated with baculovirus-derived (A) or HEK293-derived (B) fusion proteins.

Treatment of rats with a baculovirus-derived preparation of IFNβ-NAg substantially inhibited EAE induced by a subsequent encephalitogenic challenge of DHFR-NAg in CFA. Rats were administered 1 nmole of either IFNβ-NAg or NAg in saline subcutaneously on days −21, −14, and −7 followed by an encephalitogenic challenge on day 0 (Table 3). IFNβ-NAg significantly inhibited the cumulative and maximal EAE scores. This fusion protein also significantly decreased the incidence of severe paralytic disease (i.e., a partial or full hind-limb paralysis) and reduced the mean number of days afflicted by severe EAE. However, IFNβ-NAg pretreatment did not significantly modulate the day of disease onset (not shown). Rats treated with NAg alone did not show any significant attenuation of disease compared to saline-treated control rats. The time-course of disease is shown in FIG. 3A. These data show that IFNβ-NAg can be used as a pretreatment to inhibit subsequent induction of EAE. This observation demonstrates that an IFNβ-based reagent can inhibit EAE when delivered exclusively as a pre-challenge treatment regimen.

Transient transfection of HEK293 cells was used to express IFNβ-NAg (IFNβ-EK-NAg-6his) and IFN (IFNβ-EK-6his) to assess whether the NAg domain of the IFNβ-NAg fusion protein was needed for inhibition of EAE (Table 4). Again, rats were treated with 1 nmole of the fusion proteins or NAg on days −21, −14, and −7 followed by an encephalitogenic challenge on day 0. IFNβ-NAg significantly inhibited the cumulative and maximal disease scores, decreased the incidence of severe EAE, and reduced the mean number of days rats were afflicted by severe paralysis. In contrast, IFN-β was without activity and did not measurably affect the course of EAE (FIG. 3B). Thus, when treatment was completed one week before encephalitogenic challenge, IFN-β did not persist to have any enduring effect on EAE. These results suggest that a synergistic activity of IFNβ and NAg resulted in modulation of EAE.

Concerted Cytotoxic Action of IFNβ and NAg.

Figure 4:
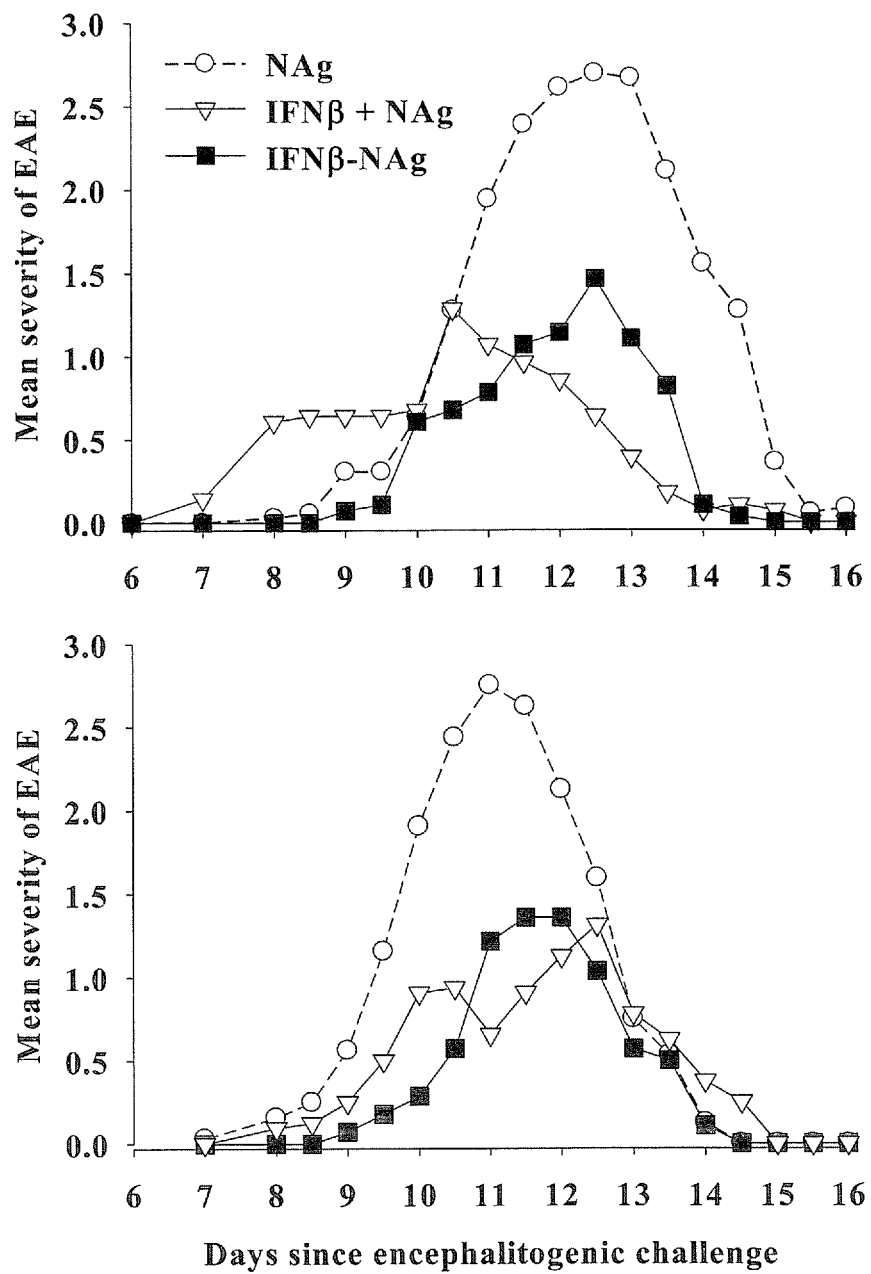
FIG. 4. A mixture of IFN-β and NAg had tolerogenic activity equal to that of the IFNβ-NAg fusion protein for inhibiting a subsequent encephalitogenic challenge. Shown are the time-courses of EAE for experiments 1 (A) and 2 (B) of Table 5.

Previous studies of IL2-NAg and NAg-IL16 fusion proteins showed that covalent linkage of the cytokine and NAg domains was involved in the inhibition of EAE (Mannie et al. 2007b; Mannie et al. 2007c and WO/2008130382). That is, administration of a fused cytokine-NAg protein was tolerogenic whereas administration of cytokine and NAg as separate molecules to the same inoculation site was without activity. To assess whether covalent linkage of IFN-β and NAg was necessary for the inhibitory activity of IFNβ-NAg, rats were injected either with IFNβ-NAg or with the combination of IFN-β and NAg as separate molecules (Table 5 and FIG. 4). Treatments were administered on days −21, −14, and −7 followed by an encephalitogenic challenge on day 0. Unlike what was observed for the IL2-NAg and NAg-IL16 fusion proteins, IFNβ-NAg treatment or the combined treatment (IFN-β+NAg) were both equally effective for inhibition of EAE. Either treatment reduced cumulative and maximal scores and decreased the duration of severe paralytic EAE. This finding distinguished the tolerogenic mechanism of IL2-NAg and NAg-IL16 from that of IFNβ-NAg due to the differential observation regarding the covalent linkage of cytokine and NAg. The tolerogenic activity of IFNβ-NAg appeared to require presentation of the relevant antigen in lymphatic tissues conditioned by IFN-β but did not require a strict intramolecular linkage of cytokine and NAg.

Figure 5:
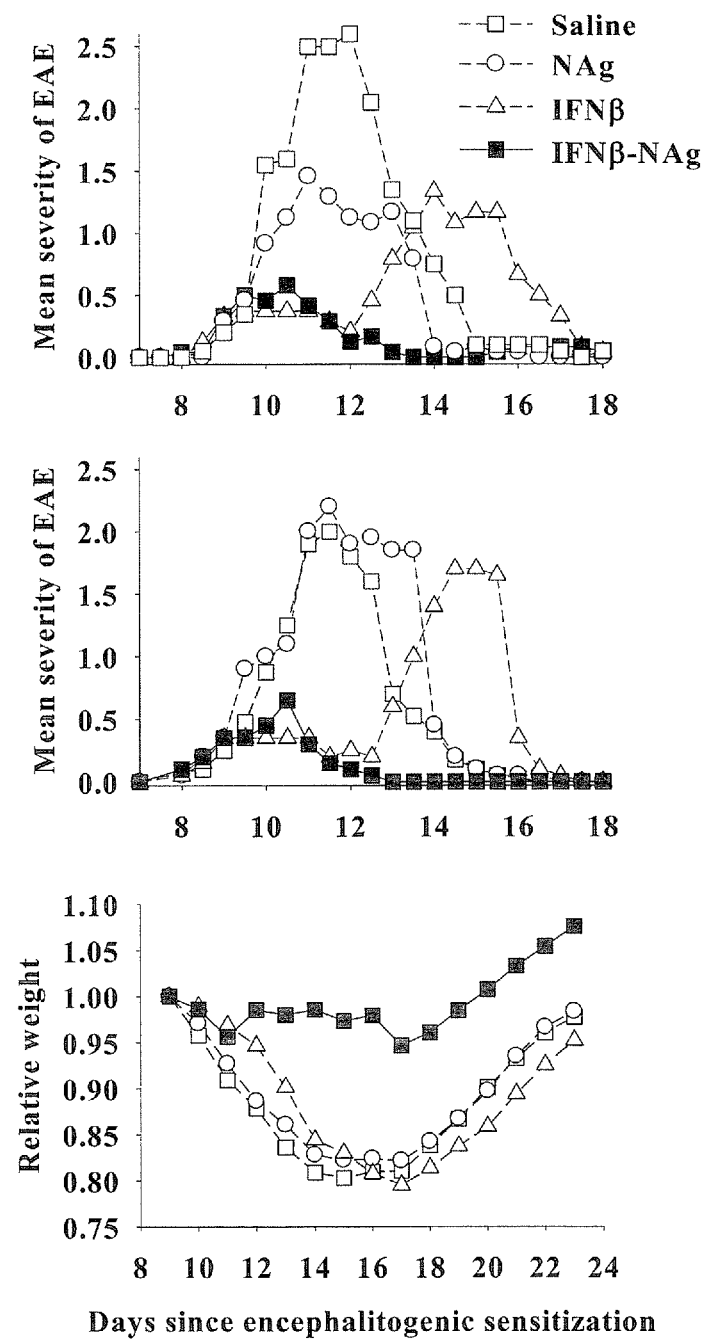
FIG. 5. The IFNβ-NAg fusion protein was more active than IFN-β for treatment of active disease. Shown are the disease time-courses for experiments 1 (A) and 2 (B) of Table 6. Also shown is the time-course of percent weight loss for experiment 2 (C).

IFNβ-NAg fusion proteins were used to treat ongoing EAE. To assess whether the IFNβ-NAg fusion protein would inhibit ongoing EAE when treatment with IFNβ-NAg was initiated after disease onset (Table 6), rats were matched for clinical intensity of EAE on day 9 after encephalitogenic challenge. Matched groups of rats were treated with IFNβ-NAg or controls on days 9, 10, and 12 (experiment 1) or on days 9, 10, 12, and 14 (experiment 2). IFNβ-NAg treatment substantially inhibited the cumulative and maximal disease scores, decreased the incidence of severe EAE, and reduced the number of days rats were afflicted with severe paralytic EAE. Rats treated with IFNβ alone showed an initial suppression of EAE (FIG. 5). However, cessation of IFNβ treatment on day 12 (FIG. 5A) or day 14 (FIG. 5B) was associated with disease rebound to the extent that no significant depression of overall disease was noted for IFNβ-treated rats (Table 6). Disease scores for rats treated with NAg alone were not significantly different from the EAE scores of rats treated with saline. The effect of these treatment modalities on EAE severity were mirrored by parallel changes in the percent maximal weight loss. For example, the time course of weight loss correlated closely with the EAE time-course and maximal disease scores (experiment 2 of Table 6 and FIGS. 5B & 5C). Based on these data, IFNβ-NAg was also an effective inhibitor of EAE when delivered after onset of EAE.

Figure 6:
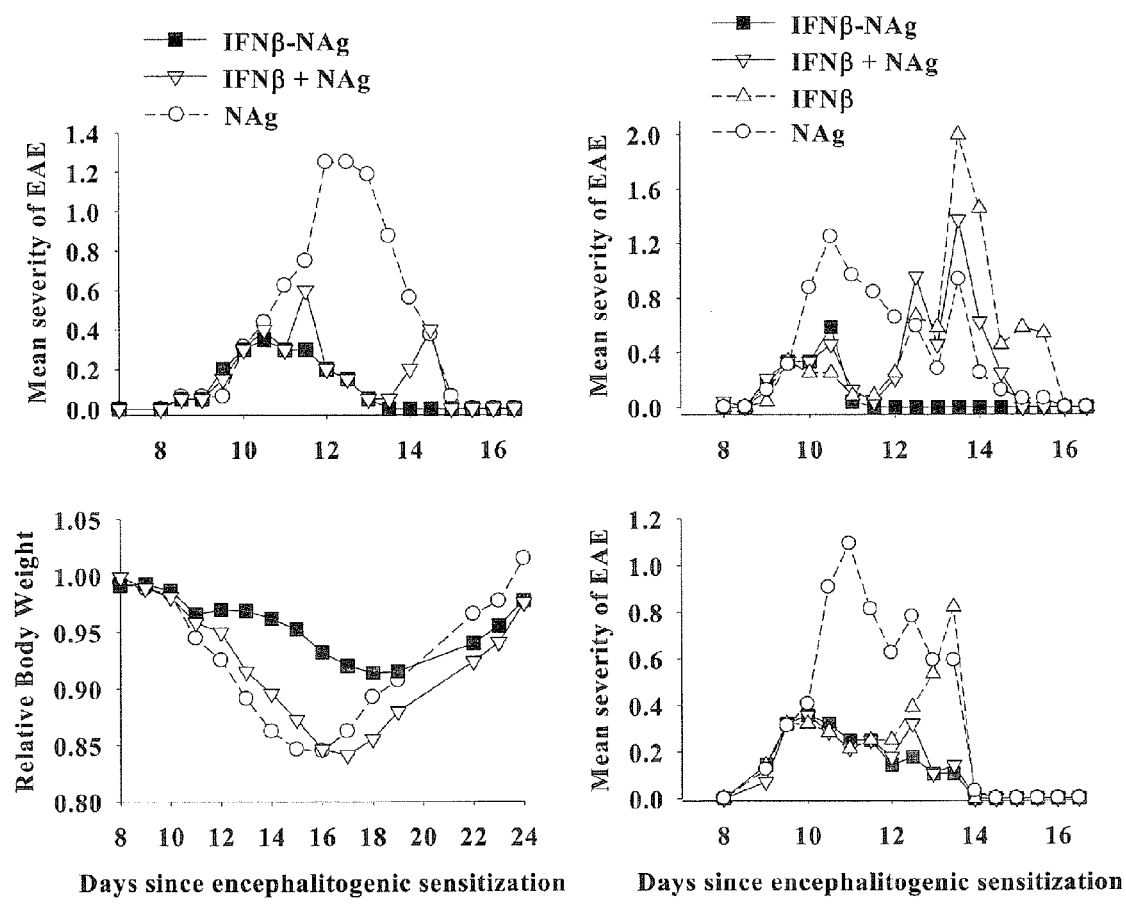
FIG. 6. The IFNβ-NAg fusion protein was a more consistent inhibitor of active disease than the combination of IFN-β and NAg. Shown are the time-courses of EAE and percent weight loss for experiment 1 (A & B) as well as the EAE time-courses for experiments 2 (C) and 3 (D) of Table 7.

Three experiments were performed to assess whether the covalent linkage between IFN-β and NAg was necessary for effective treatment of active disease. The compiled data is shown in Table 7 and the respective disease time-courses are shown in FIGS. 6A, C, and D. In all three experiments, treatment with IFNβ-NAg was highly effective in halting progression of EAE and resulted in reduced cumulative and maximal scores, a lower incidence of severe EAE, and a reduced duration of severe EAE. The pooled administration of IFN and NAg was also effective in blunting progression of EAE as assessed by the same disease measures. However, the IFNβ-NAg fusion protein was more consistent than the combination of cytokine and NAg (experiment 2, FIG. 6C). Analysis of the three experiments together (Table 7) supported the following rank order of activity: the IFNβ-NAg fusion protein≥a mixture of IFN-β+NAg>IFN-β>NAg. Possibly, the two treatment modalities [IFNβ-NAg vs (IFN-β+NAg)] appear equal during less aggressive disease due to the plateau effect of full recovery, whereas the fusion protein may have superior activity in blocking a more aggressive attack. Analysis of weight loss supported this proposition. In all three experiments of Table 7, the IFNβ-NAg fusion protein was more effective in preventing EAE-associated weight loss than the combined IFN-β and NAg treatment (experiment 1, mean=9.7% vs 16.7%, p=0.0387; experiment 2, mean=8.7% vs 15.1%, p=0.0042; experiment 3, mean=8.5% vs 13.2%, p=0.0407; unpaired t-test). Even when IFNβ-NAg and the combined IFN-β+NAg treatment both fully blocked progression of EAE (experiment 1, FIG. 6A), the IFNβ-NAg had superior activity in preventing weight loss (FIG. 6B).

Figure 7:
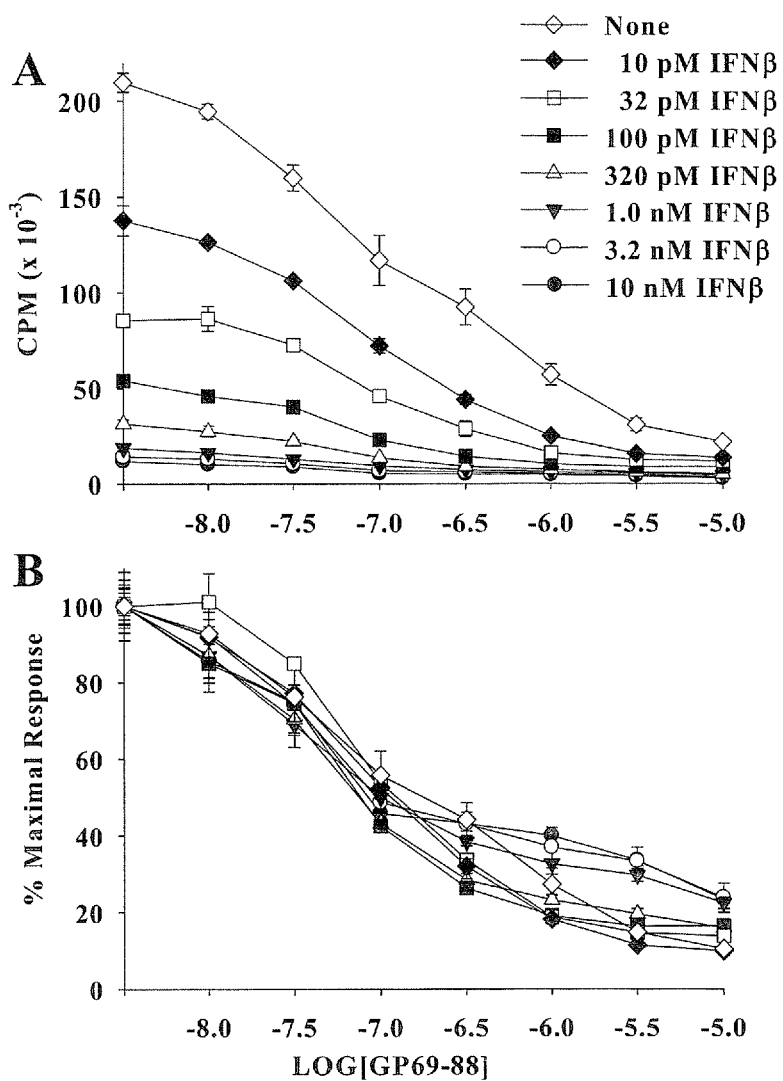
FIG. 7. IFN-β and NAg cooperatively abrogated IL-2 dependent expansion of activated T cells. An assay of fratricidal T cell-mediated killing was used to measure cytotoxic activity of IFN-β and NAg (Patel, D. M., R. W. Dudek, and M. D. Mannie. 2001. Intercellular exchange of class II MHC complexes: ultrastructural localization and functional presentation of adsorbed I-A/peptide complexes. *Cell Immunol* 214:21-34). The MHC-II$^+$ line of R1T.A cells was cultured in IL-2 supplemented medium with irradiated RsL.11 T cells (NAg-specific responders) together with designated concentrations of IFN-β and NAg. Cultures were pulsed with [$^3$H]thymidine during the last day of a 3-day culture.

The mechanism of cooperative action of IFNβ and NAg may reflect cytotoxic actions of the two reagents acting in concert. This possibility was directly supported by experiments measuring antigen-dependent T cell fratricide (FIG. 7). The IL-2 dependent, MHC-II+ clone of R1T T cells was cultured with IL-2 and irradiated MBP-specific RsL.11 responders together with designated concentrations of IFN and NAg. As shown in previous studies (Mannie et al. 2007c), IL-2 stimulates proliferation of R1T (but not the irradiated responders). In the presence of antigen, R1T APC were killed by responders during MHC-II-restricted antigen presentation thereby resulting in diminished IL-2 dependent growth. As shown in FIG. 7A, IFN-β inhibited growth of R1T cells across a concentration range of 10 pM to 10 nM, and NAg also inhibited R1T growth across a concentration range of 10 nM to 10 uM. When IFN-β and NAg were combined in the same culture, the inhibitory effects were cooperative. Normalization of these data showed that the NAg had essentially the same inhibitory activity in the presence of each IFN-β concentration (FIG. 7B). Vice versa, IFN-β had essentially the same proportional inhibitory activity in the presence of each NAg concentration (not shown). We conclude that IFN-β and NAg stimulated independent cytotoxic mechanisms that acted in concert to abrogate this T cell response.

Example 3

Tolerogenic Adjuvant Therapy

Several rat models of autoimmune disease will be used to assess activity of cytokine-antigen fusion proteins as tolerogens, and IFN-β will be tested as a tolerogenic adjuvant in each model (Table 8). Co-administration of the autoimmune self-antigen and the autoimmune cytokine, such as IFN-β, (as separate molecules) will be assessed for the ability to facilitate induction of tolerance and thereby protect against the subsequent induction of an autoimmune disease. In parallel, co-administration of tolerogenic vaccine fusion proteins and autoimmune cytokines as separate molecules will be assessed for the ability to facilitate induction of tolerance and thereby protect against a subsequent autoimmune disease. These experiments will provide insight into whether autoimmune cytokines possess efficacy as a tolerogenic adjuvant in a number of different autoimmune diseases. This information may provide a foundation for use of autoimmune cytokines as a combination treatment in multiple sclerosis. In particular, this information may also lead to the use of cytokines such as IFN-β as part of a combination treatment for other human autoimmune diseases.

Lewis Rat EAE Model.

The model of EAE in Lewis rats ($RT1^l$) has been used to provide important insight into mechanisms responsible for regulation of immune responses to "self" antigens and have been extensively used to test new therapeutic approaches for prevention and treatment of disease. The main advantages of studying EAE in Lewis rats include the sensitivity of rats to relatively limited doses of encephalitogen and the reliability of obtaining severe paralytic disease in nearly 100% of immunized animals. Day of onset is usually 9 to 12 days after encephalitogenic immunization. The disease progresses from loss of tail tonicity to hind limb paralysis, and most rats spontaneously recover by 15 to 20 days post immunization. The pattern of acute onset and spontaneous recovery resemble exacerbations and remissions seen in multiple sclerosis (MS).

Lewis Rat EAN Model.

The model of experimental autoimmune neuritis (EAN) in Lewis rats provides an important model for the Guillain Barré syndrome. Whereas EAE primarily is an autoimmune attack against CNS myelin, EAN consists of an autoimmune attack against peripheral myelin. Like EAE in Lewis rats, EAN occurs as a monophasic disease. EAN will be induced in Lewis rats by use of a neuritogenic peptide of the peripheral myelin protein P2 (P2 peptide 53-81). Tolerogenic fusion proteins will be derived that incorporate the P2(53-78) myelin peptide, and these fusion proteins will be used to prevent disease in the presence or absence of IFN-β.

Brown Norway (BN) Rat EAE Model.

The BN ($RT1^n$) rat model of EAE can be used to study pathogenic antibodies in EAE. BN rat strains mount cellular and humoral responses to the N-terminal extracellular domain of rat myelin oligodendrocyte glycoprotein (MOG).

Humoral immune responses against the extracellular domain of MOG result in demyelinating antibodies specific for conformational epitopes that are stabilized by a single intrachain disulfide linkage. Cell-mediated inflammation of the CNS enables entry of demyelinating MOG-specific antibody into the CNS to cause extensive demyelination and severe neurological signs of EAE. The consequence is severe demyelinating disease ranging from an acute fulminant course to a chronic relapsing or chronic progressive course. This model allows one to study synergy of cellular and humoral effector systems as the pathogenic basis of the demyelinating plaques in MS.

Lewis Rat EAM Model.

The research will focus on a defined myocarditic epitope (residues 1052-1073) of cardiac myosin. This peptide of cardiac myosin is "myocarditogenic" and is known to cause experimental autoimmune myocarditis (EAM) in Lewis rats. This myocarditic antigen (MAg) will be expressed as part of a tolerogenic fusion protein to test whether these fusion proteins will have tolerogenic activity against actively-induced EAM. Co-administration of IFN-β will test whether this cytokine acts as a tolerogenic adjuvant for either the myocarditic peptide or the relevant fusion proteins. The significance of the research will be (a) to establish a model of acute inflammatory heart disease, (b) to test the efficacy of a tolerogenic vaccine in EAM, and (c) to gain a basic understanding of whether IFN-β can synergistically be used to antagonize myocardial inflammation. Understanding immunologic inflammation of the cardiovascular system will be key to any fundamental advance in understanding atherosclerosis, arteriosclerosis, myocarditis, vasculitis, and a host of other cardiovascular diseases.

The generality of tolerogenic vaccines in a species other than the rat will also be tested. More specifically, mouse EAE models can be used to test whether mouse IFN-β exhibits tolerogenic activity when combined with autoantigen or with cytokine-neuroantigen fusion proteins. Evidence of generalized efficacy in different mammalian systems would provide an important foundation for the prediction that cytokine-NAg fusion proteins may be beneficial in human autoimmune disease.

Tolerogenic vaccines will be tested in two murine models of EAE. The C57BL/6 (MOG35-55) and SJL (PLP139-155) murine EAE models offer significant advantages in cost, practicality, and experimental design. Importantly, insightful mechanistic studies can be pursued in mouse EAE due to availability of many genetically altered strains. Another major advantage is that these mouse models exhibit chronic and/or relapsing-remitting disease whereas Lewis rats exhibit acute monophasic disease. Expression systems have been derived and the purified murine cytokine-NAg fusion proteins are listed in Table 9. These fusion proteins incorporate either "no neuroantigen," the murine MOG35-55 peptide of myelin oligodendrocyte glycoprotein, or the murine PLP139-155 peptide of proteolipid protein.

In vitro assays will be used to confirm the optimal construction of these fusion proteins. Both the cytokine and antigenic domains will be assessed in suitable bioassays. To assess the cytokine domain of each fusion protein, the fusion protein will be compared side by side with the isolated cytokine in a cytokine-specific bioassay. Murine GMCSF fusion proteins will be tested in bone marrow proliferative assays, IFN-β fusion proteins will be tested in T cell cytotoxicity assays, and IL-2 will be tested in T cell mitogenesis assays. To assess the antigenic domain, MOG-specific and PLP-specific T cell lines (or sensitized lymph node cells) will be used to test the in vitro activity of these fusion proteins. Fusion proteins will be compared to MOG35-55 and PLP139-155 synthetic peptides at concentrations of 1 pM to 10 uM in the presence of MOG- or PLP-specific T cells and irradiated APC. This analysis will reveal whether the NAg domain in the fusion protein is efficiently processed and presented to support T cell antigen recognition.

The experiments shown in Table 10 will be used to test the tolerogenic efficacy of the mouse fusion proteins and whether these fusion proteins or encephalitogenic peptides act in concert with IFN-β☐☐

Example 4

Tolerogenic Adjuvant Therapy in SJL (PLP139-151) Murine EAE Models

Murine Interferon-Beta/Proteolipid Protein (PLP) 139-151 Fusion Protein (IFNβ-NAg) Ameliorated a Subsequent Bout of EAE in SJL Mice.

Figure 8:
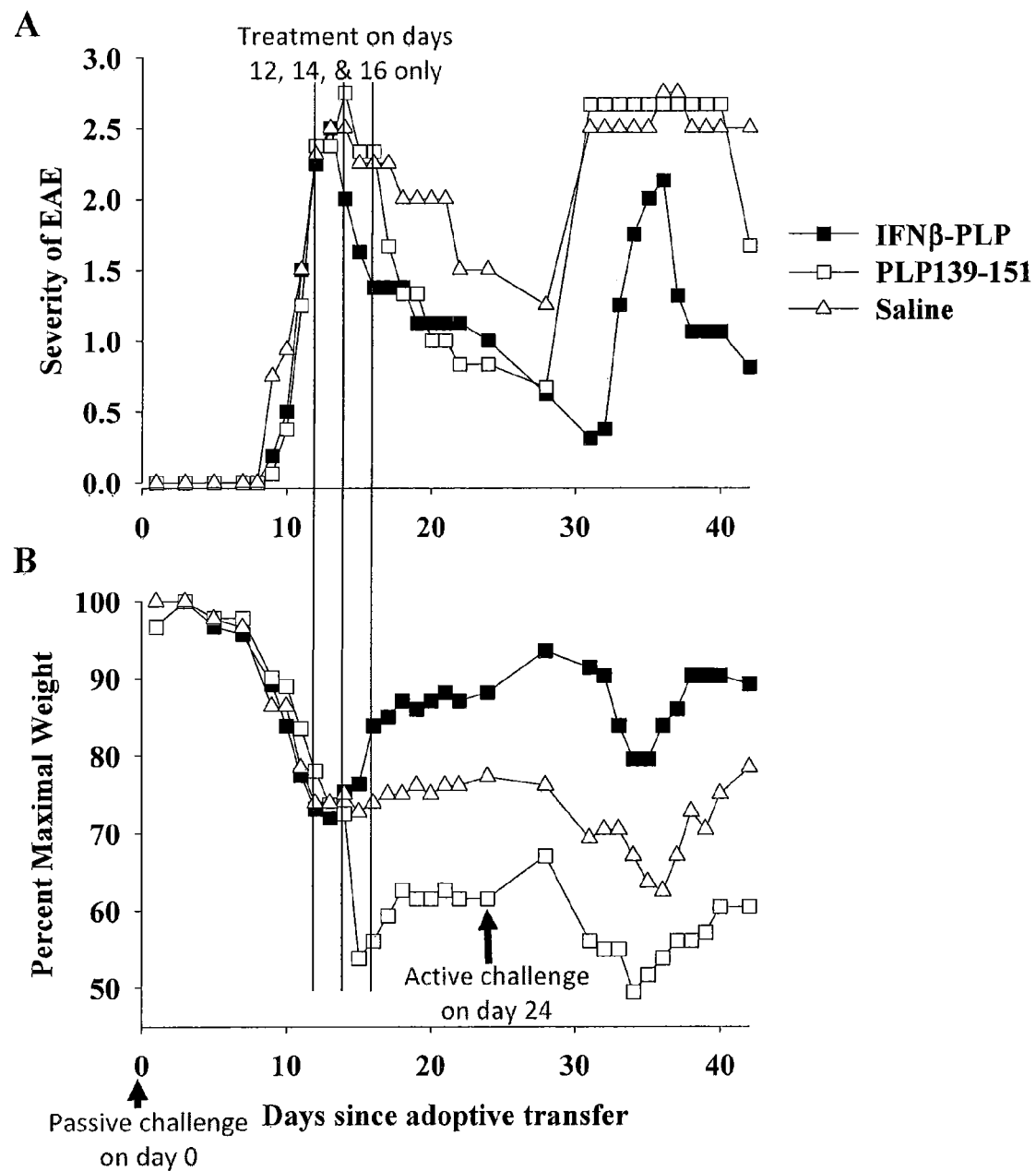
FIG. 8. Murine interferon-beta/proteolipid protein (PLP) 139-151 fusion protein (IFNβ-NAg) ameliorated a subsequent bout of EAE in SJL mice. Shown are the time-courses of EAE (A) and the percent maximal weight (B) from example 4.

On day 0, mice were passively challenged with activated, encephalitogenic T cells specific for the PLP139-151 epitope. On day 9, recipient mice began exhibiting clinical paralytic signs of EAE. On day 12, three groups of mice were matched for clinical severity. On days 12, 14, and 16, mice were treated with the IFNβ-NAg fusion protein (2 nanomoles), a synthetic PLP139-151 peptide (2 nanomoles), or saline. Treatments were given by subcutaneous injections of proteins or peptides in saline. On day 24, mice were actively challenged to induce a second bout of EAE by challenge with 200 micrograms of PLP139-151 in Complete Freund's Adjuvant. The data indicated that the IFNβ-NAg fusion protein acutely reversed EAE-associated cachexia (FIG. 8B). Furthermore, the fusion protein promoted a tolerogenic effect that ameliorated the subsequent bout of EAE (FIG. 8A). These observations support the concept that the IFNβ-NAg fusion protein may have clinical activities conducive for the treatment of autoimmune demyelinating disease of the central nervous system.

In summary, IFN-β was highly effective as a tolerogenic fusion partner or as a tolerogenic adjuvant and was used in concert with an encephalitogenic myelin antigen to constitute an effective tolerogenic vaccine for prevention and treatment of EAE providing a new platform for developing antigen-specific, cytokine-based therapies for immunological disorders such as multiple sclerosis.

TABLE 1

| Amino Acids | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |

TABLE 1-continued

| Amino Acids | | | Codons |
|---|---|---|---|
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

TABLE 2

Rat IFNβ-NAg fusion proteins

| Used in Tables 3-7 | Name used in Tables 3-7 | N- to C-terminal order of domains [a] | Biological activity of IFNβ in expression supernatants |
|---|---|---|---|
| yes | IFNβ-NAg | ss-IFNβ-EK-NAg-6his | Potent activity |
| yes | IFNβ | ss-IFNβ-EK-6his | Potent activity |
| no | | ss-IFNβ-NAg-6his | Weak activity |
| no | | ss-IFNβ-6his | Weak activity |
| no | | ss-IFNβ | Potent activity |
| no | | ss-6his-NAg-IFNβ | Weak activity |

[a] ss-native signal sequence of rat IFNβ (MANRWTLHIAFLLCFSTTALS) (SEQ ID NO: 6); IFNβ-rat interferon beta cytokine (accession numbers NP_062000); EK, enterokinase linker (GDDDDKG) (SEQ ID NO. 1); NAg-neuroantigen (the encephalitogenic 73-87 peptide of MBP; PQKSQR-SQDENPWH) (SEQ ID No. 2); 6his-6 histidine sequence. The NAg in the native 'ss-IFNβ-NAg-6his' and 'ss-6his-NAg-IFNβ' had a native 4 amino acid extension at the N-terminus (YGSLPQKSQRSQDENPWH) (SEQ ID NO: 7), which does not affect encephalitogenic activity. The term 'NAg' also refers to the synthetic gp69-88 peptide (YGSLPQKSQRSQDENPWHF) (SEQ ID NO. 5). The NAg in all cases contains the full length encephalitogenic determinant of MBP (PQKSQRSQDENPV) (SEQ ID NO: 8) in Lewis rats (Mannie, M. D., P. Y. Paterson, D. C. U'Prichard, and G. Flouret. 1990. The N- and C-terminal boundaries of myelin basic protein determinants required for encephalitogenic and proliferative responses of Lewis rat T cells. J. Neuroimmunol. 26:201-21143).

TABLE 3

The IFNβ-NAg fusion protein ameliorates a subsequent encephalitogenic challenge

| Treatment[a] | Incidence of EAE | Mean cumulative score[b] | Median cumulative score[b] | Mean maximal score[b] | Median maximal score[b] | Incidence of severe EAE[c] | Mean # days with severe EAE[c] |
|---|---|---|---|---|---|---|---|
| Saline | 13 of 13 | 9.8 ± 2.4 | 9.3 | 2.9 ± 0.3 | 3.0 | 13 of 13 | 3.2 ± 0.8 |
| NAg | 15 of 15 | 8.4 ± 2.7 | 8.5 | 2.7 ± 0.6 | 3.0 | 14 of 15 | 2.6 ± 1.1 |
| IFNβ-NAg | 9 of 9 | 3.4 ± 2.7 | 2.5 | 1.4 ± 0.9 | 1.0 | 4 of 9 | 1.0 ± 1.3 |

[a] Rats were pretreated with saline (1st row), with 1 nmole NAg (synthetic peptide gp69-88) in saline (2nd row), or with 1 nmole of IFNβ-NAg in saline (3rd row) on days −21, −14, and −7 and were challenged with 50 ug DHFR-NAg in CFA on day 0. EAE was scored at 24 hour intervals.
[b] The time-course of clinical signs is shown in FIG. 3A. The mean and median cumulative scores and the mean and median maximal scores of rats pretreated with IFNβ-NAg were significantly less than the respective scores for rats treated with NAg or saline (p ≤ 0.001).
[c] The incidence of severe EAE was scored as the incidence of EP or P (partial or full hindlimb paralysis). The incidence of severe EAE in rats pretreated with IFNβ-NAg was significantly less than the incidence in rats treated with saline (p = 0.0048) or NAg (p = 0.0147). The mean number of days afflicted with severe EAE in rats pretreated with IFNβ-NAg was significantly less than those for rats treated with saline (p < 0.001) or NAg (p = 0.003).

TABLE 4

Vaccination with the IFNβ-NAg fusion protein prevented the subsequent induction of EAE

| Exp. No. | Treatment[a] | Incidence of EAE | Mean cumulative score[b] | Median cumulative score[b] | Mean maximal score[b] | Median maximal score[b] | Incidence of severe EAE[b] | Mean # days with severe EAE[b] |
|---|---|---|---|---|---|---|---|---|
| 1 | NAg | 4 of 4 | 18.1 ± 1.8 | 18.1 | 3.0 ± 0.0 | 3.0 | 4 of 4 | 2.8 ± 0.3 |
|   | IFNβ | 4 of 4 | 22.0 ± 2.6 | 21.3 | 3.0 ± 0.0 | 3.0 | 4 of 4 | 3.0 ± 0.4 |
|   | IFNβ-NAg | 4 of 4 | 6.3 ± 6.7 | 3.9 | 1.3 ± 1.2 | 1.0 | 1 of 4 | 0.6 ± 1.3 |
| 2 | NAg | 4 of 4 | 23.0 ± 3.8 | 22.0 | 3.0 ± 0.0 | 3.0 | 4 of 4 | 3.6 ± 0.6 |
|   | IFNβ | 4 of 4 | 23.7 ± 5.3 | 23.6 | 2.8 ± 0.5 | 3.0 | 4 of 4 | 3.9 ± 0.9 |
|   | IFNβ-NAg | 4 of 4 | 7.8 ± 4.3 | 8.9 | 1.6 ± 0.8 | 2.0 | 3 of 4 | 1.0 ± 0.7 |
| 1 & 2 | NAg | 8 of 8 | 20.5 ± 3.8 | 20.0 | 3.0 ± 0.0 | 3.0 | 8 of 8 | 3.2 ± 0.7 |
|   | IFNβ | 8 of 8 | 22.8 ± 4.0 | 22.5 | 2.9 ± 0.4 | 3.0 | 8 of 8 | 3.4 ± 0.8 |
|   | IFNβ-NAg | 8 of 8 | 7.0 ± 5.3 | 5.9 | 1.5 ± 0.9 | 1.5 | 4 of 8 | 0.8 ± 1.0 |

[a]Rats were pretreated with 1 nmole NAg in saline (1st row), with 1 nmole of IFNβ in saline (2nd row), or with 1 nmole IFNβ-NAg in saline (3rd row) on days −21, −14, and −7 and were challenged with 50 ug DHFR-NAg in CFA on day 0. Rats were scored twice a day approximately 12 hours apart through day 18 and then once a day through day 28.

[b]The time-course of clinical signs from combined data of experiments 1-2 are shown in FIG. 3B and were compiled for statistical analysis. The mean and median cumulative or maximal scores of rats pretreated with IFNβ-NAg were significantly less than the respective scores for rats treated with IFNβ or NAg ($p \leq 0.001$). The incidence of severe EAE (partial or full hindlimb paralysis) in rats pretreated with IFNβ-NAg (4 of 8) was significantly less than the combined incidence of severe EAE in rats treated with IFNβ or NAg (16 of 16; $p = 0.0066$). The mean number of days afflicted with severe EAE in rats pretreated with IFNβ-NAg was significantly less than those for rats treated with IFNβ or NAg ($p < 0.001$).

TABLE 5

Covalent linkage of IFNβ and NAg is not needed to prevent EAE

| Exp | Treatment[a] | Incidence of EAE | Mean cum. score[b] | Median cum. score[b] | Mean maximal score[b] | Median maximal score[b] | % mean maximal weight loss[b] | Incidence of severe EAE[b] | Mean # days with severe EAE[b] |
|---|---|---|---|---|---|---|---|---|---|
| 1 | NAg | 9 of 9 | 20.7 ± 2.8 | 20.5 | 3.0 ± 0.0 | 3.0 | 19.2 ± 2.3 | 9 of 9 | 3.2 ± 0.4 |
|   | IFNβ + NAg | 7 of 7 | 9.0 ± 5.9 | 8.8 | 2.0 ± 1.1 | 2.0 | 14.6 ± 2.6 | 5 of 7 | 1.2 ± 1.1 |
|   | IFNβ-NAg | 7 of 7 | 8.0 ± 6.3 | 7.0 | 1.5 ± 1.0 | 2.0 | 14.8 ± 1.9 | 4 of 7 | 1.1 ± 1.2 |
| 2 | NAg | 8 of 8 | 17.0 ± 2.9 | 17.0 | 3.0 ± 0.0 | 3.0 | 16.5 ± 6.8 | 8 of 8 | 2.7 ± 0.5 |
|   | IFNβ + NAg | 8 of 8 | 8.8 ± 4.9 | 8.5 | 2.1 ± 1.1 | 2.5 | 10.9 ± 5.0 | 5 of 8 | 1.2 ± 1.2 |
|   | IFNβ-NAg | 7 of 7 | 7.2 ± 6.4 | 3.0 | 1.5 ± 1.4 | 0.5 | 10.5 ± 3.6 | 3 of 7 | 0.9 ± 1.2 |
| 1-2 | NAg | 17 of 17 | 19.0 ± 3.3 | 18.8 | 3.0 ± 0.0 | 3.0 | 17.9 ± 5.0 | 17 of 17 | 3.0 ± 0.5 |
|   | IFNβ + NAg | 15 of 15 | 8.9 ± 5.2 | 8.8 | 2.0 ± 1.0 | 2.0 | 12.6 ± 4.4 | 10 of 15 | 1.2 ± 1.1 |
|   | IFNβ-NAg | 14 of 14 | 7.6 ± 6.2 | 5.5 | 1.5 ± 1.1 | 1.5 | 12.6 ± 3.6 | 7 of 14 | 1.0 ± 1.2 |

[a]For experiments 1 and 2, rats were pretreated with 1 nmole NAg (1st row), with separate injections of 1 nmole NAg and 1 nmole IFNβ at a distance of <0.5 cm apart near the base of the tail (IFNβ + NAg; 2nd row), or with 1 nmole of IFNβ-NAg (3rd row) on days −21, −14, and −7. All injections were subcutaneous in saline. Rats were challenged with 50 ug DHFR-NAg in CFA on day 0. EAE was scored at 12 hour intervals.

[b]The time-course for experiments 1 and 2 are shown in FIG. 4A and 4B, respectively, and were compiled for statistical analysis. For rats treated with the combination of IFNβ + NAg or the IFNβ-NAg fusion protein, the mean and median cumulative scores ($p < 0.001$, $p < 0.001$), the mean ($p = 0.013$, $p < 0.001$) and median ($p = 0.005$, $p < 0.001$) maximal scores, the mean percent weight loss ($p = 0.003$, $p = 0.003$), the incidence of severe EAE ($p = 0.0149$, $p = 0.0013$) and the mean number of days with severe EAE ($p < 0.001$, $p < 0.001$) were significantly less than the respective scores for rats treated with NAg.

TABLE 6

Treatment with the IFNβ-NAg fusion protein halts progression of clinical EAE.

| Experiment | Treatment[a] | Mean cum. score[b] | Median cum. score[b] | Mean maximal score[b] | Median maximal score[b] | % mean maximal weight loss[b] | Incidence of severe EAE[b] | Mean # days with severe EAE[b] |
|---|---|---|---|---|---|---|---|---|
| 1 | Saline | 17.6 ± 3.0 | 19.5 | 3.0 ± 0.0 | 3.0 | 14.5 ± 2.9 | 5 of 5 | 2.6 ± 0.6 |
|   | NAg | 10.0 ± 4.9 | 11.9 | 2.1 ± 1.4 | 2.0 | 11.5 ± 4.1 | 4 of 6 | 1.4 ± 1.1 |
|   | IFNβ | 11.1 ± 5.1 | 10.3 | 2.2 ± 0.8 | 2.0 | 10.6 ± 5.3 | 5 of 6 | 1.4 ± 1.1 |
|   | IFNβ-NAg | 3.4 ± 2.1 | 3.5 | 0.7 ± 0.6 | 0.5 | 3.8 ± 2.0 | 1 of 6 | 0.1 ± 0.2 |
| 2 | Saline | 17.6 ± 3.9 | 17.3 | 3.0 ± 0.0 | 3.0 | 20.3 ± 1.8 | 7 of 7 | 2.5 ± 0.7 |
|   | NAg | 16.7 ± 3.2 | 17.5 | 3.0 ± 0.0 | 3.0 | 18.4 ± 1.3 | 5 of 5 | 2.2 ± 0.8 |
|   | IFNβ | 11.2 ± 5.9 | 8.3 | 2.0 ± 1.0 | 2.0 | 20.7 ± 1.9 | 3 of 5 | 1.3 ± 1.4 |
|   | IFNβ-NAg | 2.7 ± 1.5 | 2.3 | 0.7 ± 0.8 | 0.3 | 6.4 ± 5.0 | 1 of 5 | 0.1 ± 0.2 |
| 1 & 2 | Saline | 17.6 ± 3.4 | 18.0 | 3.0 ± 0.0 | 3.0 | 17.9 ± 3.7 | 12 of 12 | 2.6 ± 0.6 |
|   | NAg | 13.1 ± 5.4 | 12.8 | 2.5 ± 1.1 | 3.0 | 14.6 ± 4.7 | 9 of 11 | 1.8 ± 1.0 |

TABLE 6-continued

Treatment with the IFNβ-NAg fusion protein halts progression of clinical EAE.

| Experiment | Treatment[a] | Mean cum. score[b] | Median cum. score[b] | Mean maximal score[b] | Median maximal score[b] | % mean maximal weight loss[b] | Incidence of severe EAE[b] | Mean # days with severe EAE[b] |
|---|---|---|---|---|---|---|---|---|
| | IFNβ | 11.1 ± 5.2 | 8.3 | 2.1 ± 0.8 | 2.0 | 15.2 ± 6.5 | 8 of 11 | 1.4 ± 1.2 |
| | IFNβ-NAg | 3.1 ± 1.8 | 2.8 | 0.7 ± 0.7 | 0.5 | 5.0 ± 3.7 | 2 of 11 | 0.1 ± 0.2 |

[a]For experiments 1 and 2, rats were challenged with 50 ug DHFR-NAg in CFA on day 0. On day 9, rats were matched for clinical signs of EAE and were randomly assigned to groups that were injected subcutaneously with 1 nmole NAg, 1 nmole IFNβ, or 1 nmole IFNβ-NAg. For experiment 1, matched groups that received NAg, IFNβ, or IFNβ-NAg (n = 6, mean cumulative score = 0.33) were each comprised of 4 rats exhibiting distal limp tail (dLT; 0.25) and 2 rats exhibiting limp tail (LT; 0.5). A 4th group (n = 5; mean cumulative score of 0.2; 0.25, 0.25, 0.25, 0.25, 0) was treated with saline. Each group was treated on day 9 (1 nmole), day 10 (1 nmole), and again on day 12 (0.5 nmole). For experiment 2, matched groups that received NAg, IFNβ, or IFNβ-NAg (n = 5, mean cumulative score = 0.35) were each comprised of 3 rats exhibiting distal limp tail (dLT; 0.25) and 3 rats exhibiting limp tail (LT; 0.5). A 4th group (n = 7; mean cumulative score of 0.36; 0, 0, 0.25, 0.25, 0.5, 0.5, 1.0) was treated with saline. Each group was treated with 1 nmole on days 9, 10, 12, and 14.

[b]The disease time-course for experiments 1 and 2 are shown in FIG. 5A and 5B, respectively, and were compiled for statistical analysis. The time-course of weight loss for experiment 2 is shown in FIG. 5C. Compared to rats treated with IFNβ-NAg, the mean and median cumulative scores (p < 0.001), and mean and median maximal scores (p ≤ 0.001), and mean maximal weight loss (p < 0.001), the incidence of severe EAE (p < 0.001, p = 0.0089, p = 0.03), and the mean number of days with severe EAE (p < 0.001, p < 0.001, and p = 0.007) was significantly less than the respective values for rats treated with saline, NAg, or IFNβ, respectively. Compared to rats treated with IFNβ, the mean (p = 0.003) and median (p = 0.022) cumulative scores, the mean (p = 0.035) and median (p = 0.018) maximal EAE scores, and the mean number of days with severe EAE (p = 0.009) were significantly less than the respective scores for rats treated with saline.

TABLE 7

Treatment with IFNβ-NAg or a mixture of IFNβ and NAg attenuates active EAE.

| Experiment | Treatment[a] | Mean cum. score[b] | Median cum. score[b] | Mean maximal score[b] | Median maximal score[b] | Incidence of severe EAE[b] | Mean # days with severe EAE (A-P)[b] |
|---|---|---|---|---|---|---|---|
| 1 | NAg | 7.7 ± 4.6 | 5.9 | 1.4 ± 1.1 | 1.0 | 3 of 4 | 1.5 ± 1.1 |
| | IFNβ + NAg | 2.7 ± 3.1 | 1.5 | 0.6 ± 0.8 | 0.3 | 1 of 5 | 0.5 ± 0.9 |
| | IFNβ-NAg | 1.7 ± 0.9 | 1.8 | 0.4 ± 0.1 | 0.3 | 0 of 5 | 0.3 ± 0.7 |
| 2 | NAg | 6.9 ± 2.3 | 7.4 | 1.9 ± 0.9 | 2.0 | 7 of 8 | 1.4 ± 0.9 |
| | IFNβ | 7.2 ± 3.8 | 5.9 | 2.2 ± 1.0 | 2.5 | 6 of 6 | 1.9 ± 2.1 |
| | IFNβ + NAg | 4.8 ± 2.7 | 5.3 | 1.5 ± 0.7 | 2.0 | 5 of 6 | 1.0 ± 0.7 |
| | IFNβ-NAg | 1.0 ± 0.7 | 0.8 | 0.6 ± 0.7 | 0.4 | 1 of 6 | 0.1 ± 0.2 |
| 3 | NAg | 5.8 ± 4.4 | 4.6 | 1.6 ± 1.3 | 1.5 | 5 of 8 | 1.1 ± 1.1 |
| | IFNβ | 3.1 ± 2.2 | 2.5 | 1.0 ± 1.1 | 0.5 | 2 of 7 | 0.4 ± 0.6 |
| | IFNβ + NAg | 1.9 ± 0.7 | 1.5 | 0.4 ± 0.1 | 0.3 | 0 of 7 | 0.0 ± 0.0 |
| | IFNβ-NAg | 1.7 ± 0.6 | 1.8 | 0.4 ± 0.1 | 0.3 | 0 of 7 | 0.0 ± 0.0 |
| 1-3 | NAg | 6.6 ± 3.6 | 5.9 | 1.7 ± 1.1 | 2.0 | 15 of 20 | 1.3 ± 1.0 |
| | IFNβ | 5.0 ± 3.6 | 4.0 | 1.5 ± 1.2 | 1.0 | 8 of 13 | 1.1 ± 1.7 |
| | IFNβ + NAg | 3.1 ± 2.5 | 1.8 | 0.8 ± 0.8 | 0.4 | 6 of 18 | 0.5 ± 0.7 |
| | IFNβ-NAg | 1.4 ± 0.8 | 1.4 | 0.4 ± 0.4 | 0.3 | 1 of 18 | 0.1 ± 0.4 |

[a]DHFR-NAg sensitized rats were matched for clinical signs of EAE and were treated with 1 nmole of the following reagents; NAg, IFNβ, a mixture of IFNβ + NAg, or the IFNβ-NAg fusion protein (s.c. in saline) on days 10, 11, and 13 (experiment 1), on days 9, 10, 12, and 14 (experiment 2), or on days 9, 10, and 12 (experiment 3).
[b]The time-course of EAE for experiments 1-3 are shown in FIG. 6A, 6C, 6D respectively. The time-course of weight loss for experiment 1 is shown in FIG. 6B. The 3 experiments (last four rows of Table 7) were compiled and analyzed. Compared to rats treated with IFNβ-NAg, the mean and median cumulative scores (p ≤ 0.005), the mean and median maximal score (p ≤ 0.002), the incidence of severe EAE (p < 0.0001, p = 0.0012), the number of days with severe EAE (p = 0.001, p = 0.036) was significantly less than the respective values for rats treated with NAg or IFNβ, respectively. Compared to rats treated with the combination of IFNβ + NAg, the mean (p = 0.001) and median (p = 0.016) cumulative scores, the mean (p = 0.011) and median (p = 0.019) maximal score, the incidence of severe EAE (p = 0.021), and the mean number of days with severe EAE (p = 0.039) was significantly less than the respective values for rats treated with NAg. For these 3 experiments, severe EAE was defined by scores from 1.0 to 3.0.

TABLE 8

Experimental design for rat models of autoimmune disease (EAE, EAN, and EAM models)

| Experimental Model | Fusion protein | Assessment of synergy | Measurement |
|---|---|---|---|
| EAE (Lewis) | MBP69-88 | ±IFN-beta | Disease time-course |
| | NAgIL16 | ±IFN-beta | Auto-antibody production |
| | GMCSF-NAg | ±IFN-beta | Histological signs |
| | IFNβ-NAg | ±IFN-beta | |
| | saline | ±IFN-beta | |
| EAN (Lewis) | P2(53-78) | ±IFN-beta | Disease time-course |
| | NAgIL16 | ±IFN-beta | Auto-antibody production |
| | GMCSF-NAg | ±IFN-beta | Histological signs |
| | IFNβ-NAg | ±IFN-beta | |
| | saline | ±IFN-beta | |

TABLE 8-continued

Experimental design for rat models of autoimmune disease
(EAE, EAN, and EAM models)

| Experimental Model | Fusion protein | Assessment of synergy | Measurement |
|---|---|---|---|
| EAE (BN) | MOG(1-125) | ±IFN-beta | Disease time-course |
|  | MOG-IL16 | ±IFN-beta | Auto-antibody production |
|  | GMCSF-MOG | ±IFN-beta | Histological signs |
|  | IFNβ-MOG | ±IFN-beta |  |
|  | IL4-MOG | ±IFN-beta |  |
|  | saline | ±IFN-beta |  |
| EAM (Lewis) | Myosin(1052) | ±IFN-beta | Disease time-course |
|  | Myo-IL16 | ±IFN-beta | Auto-antibody production |
|  | GMCSF-Myo | ±IFN-beta | Histological signs |
|  | IFNβ-Myo | ±IFN-beta |  |
|  | saline | ±IFN-beta |  |

[a] Rats will be treated with 2 nanomoles of the designated fusion protein either with or without 1 nanomole of IFN-beta on days -21, -14, and -7. Rats will then be immunized with synthetic peptide gp69-88 (20 nmoles/rat) of guinea pig myelin basic protein in CFA to induce EAE, with the P2(53-78) peptide (80 nmoles/rat) in CFA to induce EAN, with 4 nanomoles of the extracellular MOG IgV domain in CFA to induce EAE in BN rats, with cardiac myosin beta chain peptide myosin(1052-1076) (170 nmoles/rat) in CFA to induce EAM. For induction of EAM, rats will also receive 200 nanograms of Pertussis Toxin on days 0 and 2 (i.p.) and will receive a booster of myosin(1052-1076) (170 nmoles/ rat) in IFA on day 7. A total of 42 groups will be assessed at 8 rats/group with 2 experimental replications (336 rats × 2 = 672 rats).
[b] The time course of clinical signs and body weight will be measured daily for EAE and EAN. The intensity of EAM will be assessed by histological examination of cardiac inflammatory lesions at day 21 after the initial immunization. Rats will be subjected to a pre-bleed on the day before immunization and a terminal bleed on the day at the end of the experiment. ELISA will be used to assess auto-antibody production. For EAE and EAN, the spinal cord will be assessed for perivascular infiltrates and demyelination. For EAM, the cardiac tissue will be scored for inflammatory lesions.

TABLE 9

Expression systems for murine cytokine-NAg fusion proteins

| Descriptor | N to C terminal order of domains |
|---|---|
| GMCSF-MOG | GMCSF-(MOG35-55)-8his |
| GMCSF-PLP | GMCSF-(PLP139-155)-8his |
| GMCSF | GMCSF-8his |
| IFNβ-MOG | IFNβ-(MOG35-55)-8his |
| IFNβ-PLP | IFNβ-(PLP139-155)-8his |
| IFNβ | IFNβ-8his |
| IL2-MOG | IL2-(MOG35-55)-8his |

TABLE 9-continued

Expression systems for murine cytokine-NAg fusion proteins

| Descriptor | N to C terminal order of domains |
|---|---|
| IL2-PLP | IL2-(PLP139-155)-8his |
| IL2 | IL2-8his |

TABLE 10

Experimental design for mouse models of autoimmune disease
(EAE, EAN, and EAM models)

| Experimental Model | Fusion protein | Assessment of synergy | Measurement |
|---|---|---|---|
| EAE (C57BL/6) | MOG35-55 | ±IFN-beta | Disease time-course |
|  | GMCSF-NAg | ±IFN-beta | Auto-antibody production |
|  | saline | ±IFN-beta | Histological signs |
| EAE (SJL/J) | PLP139-155 | ±IFN-beta | Disease time-course |
|  | GMCSF-NAg | ±IFN-beta | Auto-antibody production |
|  | saline | ±IFN-beta | Histological signs |

[a] Mice will be treated with 2 nanomoles of the designated fusion protein either with or without 1 nanomole of IFN-beta on days -21, -14, and -7. Mice will then be immunized with synthetic peptide MOG35-55 (200 micrograms/mouse) or with the PLP139-155 peptide (100 micrograms/mouse) in CFA to induce EAE. For induction of EAE in C57BL/6 mice, mice will also receive 200 nanograms of Pertussis Toxin on days 0 and 2 (i.p.). A total of 12 groups will be assessed at 8 mice/group with 2 experimental replications (192 mice).
[b] The time course of clinical signs and body weight will be measured daily for each mouse (TABLE 11). Mice will be subjected to a pre-bleed on the day before immunization and a terminal bleed on day 21 at the end of the experiment. ELISA will be used to assess auto-antibody production. Spinal cord and brain will be assessed for perivascular infiltrates and demyelination.

TABLE 11

Scale for scoring of clinical signs in mice

| Score | Clinical Signs |
|---|---|
| 0 | no disease |
| 0.5 | partial or full paralysis of tail |
| 1.0 | ataxia |
| 2.0 | partial hindlimb paralysis |
| 3.0 | total hindlimb paralysis |
| 4.0 | total hind limb paralysis with forelimb involvement |
| 5.0 | moribund (euthanasia) |

That which is claimed is:

1. A composition comprising:
    (a) at least one fusion protein comprising, from N-terminal to C-terminal, (i) a cytokine, wherein the cytokine is interferon-β (IFN-β); (ii) optionally an enterokinase linking moiety, wherein the enterokinase linking moiety is (1) an amino acid sequence of SEQ ID NO:1, (2) an amino acid sequence having at least 80% identity or homology with the amino acid sequence of SEQ ID NO: 1, (3) an amino acid sequence encoded by a nucleic acid sequence encoding an enterokinase recognition site, or (4) an amino acid sequence encoded by a nucleic acid sequence that hybridizes with the complement of the nucleic acid sequence of (3) under stringent conditions as represented by hybridization conditions of 0.5M NaHPO$_4$, 7% sodium dodecyl sulfate (SDS), 1 mM EDTA at 65° C. and wash conditions of 0.1×SSC/0.1% SDS at 68° C.; and (iii) an autoimmune antigen, or portion thereof, wherein the autoimmune antigen is myelin basic protein (MBP);
    (b) a cytokine, wherein the cytokine is IFN-β; and
    (c) a pharmaceutically acceptable carrier, excipient or diluent.

2. A kit comprising one or more containers having pharmaceutical dosage units comprising an effective amount of the composition of claim 1 for the treatment of multiple sclerosis, wherein the container is packaged with optional instructions for the use thereof.

3. The composition of claim 1, wherein the portion of the autoimmune antigen is an encephalitogenic determinant portion of MBP, wherein the encephalitogenic determinant portion of MBP is (1) an amino acid sequence of SEQ ID NO:2, an amino acid sequence of at least 80% identity with the amino acid sequence of SEQ ID NO:2, (3) an amino acid sequence encoded by a nucleic acid sequence encoding the encephalitogenic determinant portion of MBP, or (4) an amino acid sequence encoded by a nucleic acid sequence that hydridizes with the complement of the nucleic acid sequence of (3) under stringent conditions as represented by hybridization conditions of 0.5M NaHPO$_4$, 7% sodium dodecyl sulfate (SDS), 1 mM EDTA at 65° C. and wash conditions of 0.1×SSC/0.1% SDS at 68° C.

* * * * *

UNITED STATES PATENT AND TRADEMARK OFFICE
CERTIFICATE OF CORRECTION

| | | |
|---|---|---|
| PATENT NO. | : 9,669,090 B2 | Page 1 of 1 |
| APPLICATION NO. | : 14/518705 | |
| DATED | : June 6, 2017 | |
| INVENTOR(S) | : Mannie | |

It is certified that error appears in the above-identified patent and that said Letters Patent is hereby corrected as shown below:

In the Specification

Column 27, Line 28: Please correct "commercial IFN" to read -- commercial IFNβ --

Column 28, Line 19: Please correct "and IFN (IFNβ-" to read -- and IFNβ (IFNβ- --

Column 28, Line 29: Please correct "of IFN and" to read -- of IFNβ and --
      Line 57: Please correct "of IFN" to read -- of IFNβ --

Signed and Sealed this
Sixth Day of March, 2018

Andrei Iancu
*Director of the United States Patent and Trademark Office*

SEQUENCE LISTING

```
<160> NUMBER OF SEQ ID NOS: 8

<210> SEQ ID NO 1
<211> LENGTH: 7
<212> TYPE: PRT
<213> ORGANISM: Artificial
<220> FEATURE:
<223> OTHER INFORMATION: Enterokinase (EK) linker sequence

<400> SEQUENCE: 1

Gly Asp Asp Asp Asp Lys Gly
1               5

<210> SEQ ID NO 2
<211> LENGTH: 15
<212> TYPE: PRT
<213> ORGANISM: Artificial
<220> FEATURE:
<223> OTHER INFORMATION: Encephalitogenic epitope peptide sequence of
      MBP

<400> SEQUENCE: 2
```

-continued

Pro Gln Lys Ser Gln Arg Ser Gln Asp Glu Asn Pro Val Val His
1               5                   10                  15

<210> SEQ ID NO 3
<211> LENGTH: 197
<212> TYPE: PRT
<213> ORGANISM: Homo sapiens

<400> SEQUENCE: 3

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 4
<211> LENGTH: 21
<212> TYPE: PRT
<213> ORGANISM: Homo sapiens

<400> SEQUENCE: 4

Tyr Gly Ser Leu Pro Gln Lys Ser His Gly Arg Thr Gln Asp Glu Asn
1               5                   10                  15

Pro Val Val His Phe
            20

<210> SEQ ID NO 5
<211> LENGTH: 20
<212> TYPE: PRT
<213> ORGANISM: Artificial
<220> FEATURE:
<223> OTHER INFORMATION: Synthetic gp69-88 peptide

<400> SEQUENCE: 5

Tyr Gly Ser Leu Pro Gln Lys Ser Gln Arg Ser Gln Asp Glu Asn Pro
1               5                   10                  15

Val Val His Phe

```
                            20

<210> SEQ ID NO 6
<211> LENGTH: 21
<212> TYPE: PRT
<213> ORGANISM: Rattus norvegicus

<400> SEQUENCE: 6

Met Ala Asn Arg Trp Thr Leu His Ile Ala Phe Leu Leu Cys Phe Ser
1               5                   10                  15

Thr Thr Ala Leu Ser
            20

<210> SEQ ID NO 7
<211> LENGTH: 19
<212> TYPE: PRT
<213> ORGANISM: Artificial
<220> FEATURE:
<223> OTHER INFORMATION: Encephalitogenic epitope sequence with 4 amino
      acid extension at N-terminus

<400> SEQUENCE: 7

Tyr Gly Ser Leu Pro Gln Lys Ser Gln Arg Ser Gln Asp Glu Asn Pro
1               5                   10                  15

Val Val His

<210> SEQ ID NO 8
<211> LENGTH: 13
<212> TYPE: PRT
<213> ORGANISM: Rattus norvegicus

<400> SEQUENCE: 8

Pro Gln Lys Ser Gln Arg Ser Gln Asp Glu Asn Pro Val
1               5                   10
```